US011911070B2

(12) United States Patent
Holsten et al.

(10) Patent No.: US 11,911,070 B2
(45) Date of Patent: Feb. 27, 2024

(54) SEAL ASSEMBLY WITH INTEGRAL FILTER AND EVACUATION PORT

(71) Applicant: Covidien LP, Mansfield, MA (US)

(72) Inventors: Henry Holsten, Hamden, CT (US); Kenneth Horton, South Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 540 days.

(21) Appl. No.: 17/109,333

(22) Filed: Dec. 2, 2020

(65) Prior Publication Data

US 2021/0100583 A1  Apr. 8, 2021

Related U.S. Application Data

(63) Continuation of application No. 15/876,699, filed on Jan. 22, 2018, now Pat. No. 10,874,426.

(Continued)

(51) Int. Cl.
*A61B 17/34* (2006.01)
*B01D 35/30* (2006.01)
(Continued)

(52) U.S. Cl.
CPC .......... *A61B 17/3421* (2013.01); *A61B 17/34* (2013.01); *A61B 17/3462* (2013.01);
(Continued)

(58) Field of Classification Search
CPC . A61B 17/3421; A61B 17/34; A61B 17/3462; A61B 17/3474;
(Continued)

(56) References Cited

U.S. PATENT DOCUMENTS

| 3,402,710 A | 9/1968 | Paleschuck |
| 4,447,237 A | 5/1984 | Frisch et al. |

(Continued)

FOREIGN PATENT DOCUMENTS

| AU | 2005202133 A1 | 12/2006 |
| CN | 1907513 A | 2/2007 |

(Continued)

OTHER PUBLICATIONS

Chinese Office Action dated Apr. 6, 2022, issued in corresponding CN Appln. No. 2018101341285, 8 pages.

(Continued)

*Primary Examiner* — Amber R Stiles
(74) *Attorney, Agent, or Firm* — Carter, DeLuca & Farrell LLP

(57) ABSTRACT

A seal assembly for use with an access apparatus includes an integral filter and evacuation port for filtering of fluids, e.g., smoke, from an operating site and removing contaminants and/or odor from the fluids for release of the filtered fluids into the ambient atmosphere. The seal assembly may be a separate subassembly or component which is releasably couplable to the access apparatus or may be integral with the access apparatus. The seal assembly defines its own flow path independent of the insufflation mechanism of the cannula assembly, and is capable of filtering fluids even in the presence of a surgical object positioned within the cannula assembly.

18 Claims, 18 Drawing Sheets

Related U.S. Application Data

(60) Provisional application No. 62/573,308, filed on Oct. 17, 2017, provisional application No. 62/457,511, filed on Feb. 10, 2017.

(51) Int. Cl.
*B01D 46/00* (2022.01)
*B01D 46/24* (2006.01)

(52) U.S. Cl.
CPC .......... *A61B 17/3474* (2013.01); *B01D 35/30* (2013.01); *B01D 46/0097* (2013.01); *B01D 46/2411* (2013.01); *A61B 2017/3437* (2013.01); *A61B 2218/008* (2013.01); *B01D 2271/027* (2013.01)

(58) Field of Classification Search
CPC ...... A61B 2017/3437; A61B 2218/008; A61B 18/00; A61B 17/3415; B01D 35/30; B01D 46/0097; B01D 46/2411; B01D 2271/027; B01D 46/0027; A61M 1/784; A61M 1/90; A61M 1/79; A61M 2205/7509; A61M 2205/7518; A61M 2205/7545
See application file for complete search history.

(56) References Cited

U.S. PATENT DOCUMENTS

| | | | |
|---|---|---|---|
| 4,475,548 A | 10/1984 | Muto | |
| 4,519,908 A | 5/1985 | Woodruff | |
| 4,610,665 A | 9/1986 | Matsumoto et al. | |
| 5,015,228 A | 5/1991 | Columbus et al. | |
| 5,041,095 A | 8/1991 | Littrell | |
| 5,104,389 A | 4/1992 | Deem et al. | |
| 5,127,626 A | 7/1992 | Hilal et al. | |
| 5,180,376 A | 1/1993 | Fischell | |
| 5,207,656 A | 5/1993 | Kranys | |
| 5,330,497 A | 7/1994 | Freitas et al. | |
| 5,338,313 A | 8/1994 | Mollenauer et al. | |
| 5,342,315 A | 8/1994 | Rowe et al. | |
| 5,360,417 A | 11/1994 | Gravener et al. | |
| 5,389,080 A | 2/1995 | Yoon | |
| 5,389,081 A | 2/1995 | Castro | |
| 5,391,153 A | 2/1995 | Haber et al. | |
| 5,407,434 A | 4/1995 | Gross | |
| 5,429,609 A | 7/1995 | Yoon | |
| 5,441,486 A | 8/1995 | Yoon | |
| 5,460,616 A | 10/1995 | Weinstein et al. | |
| 5,463,010 A | 10/1995 | Hu et al. | |
| 5,480,410 A | 1/1996 | Cuschieri et al. | |
| 5,484,425 A | 1/1996 | Fischell et al. | |
| 5,514,109 A | 5/1996 | Mollenauer et al. | |
| 5,514,133 A | 5/1996 | Golub et al. | |
| 5,542,931 A | 8/1996 | Gravener et al. | |
| 5,550,363 A | 8/1996 | Obata | |
| 5,556,387 A | 9/1996 | Mollenauer et al. | |
| 5,603,702 A | 2/1997 | Smith et al. | |
| 5,628,732 A | 5/1997 | Antoon, Jr. et al. | |
| 5,634,908 A | 6/1997 | Loomas | |
| 5,634,937 A | 6/1997 | Mollenauer et al. | |
| 5,653,705 A | 8/1997 | de la Torre et al. | |
| 5,662,615 A | 9/1997 | Blake, III | |
| 5,722,958 A | 3/1998 | Gravener et al. | |
| 5,722,962 A | 3/1998 | Garcia | |
| 5,738,664 A | 4/1998 | Erskine et al. | |
| 5,741,298 A | 4/1998 | MacLeod | |
| 5,743,884 A | 4/1998 | Hasson et al. | |
| 5,779,697 A | 7/1998 | Glowa et al. | |
| 5,788,676 A | 8/1998 | Yoon | |
| 5,843,031 A | 12/1998 | Hermann | |
| 5,906,577 A | 5/1999 | Beane et al. | |
| 5,957,913 A | 9/1999 | de la Torre et al. | |
| 5,989,233 A | 11/1999 | Yoon | |
| 6,017,356 A | 1/2000 | Frederick et al. | |
| 6,024,736 A | 2/2000 | de la Torre et al. | |
| 6,079,692 A | 6/2000 | Powell | |
| 6,110,154 A | 8/2000 | Shimomura et al. | |
| 6,315,770 B1 | 11/2001 | de la Torre et al. | |
| 6,319,246 B1 | 11/2001 | de la Torre et al. | |
| 6,355,014 B1 | 3/2002 | Zadno-Azizi et al. | |
| 6,440,063 B1 | 8/2002 | Beane et al. | |
| 6,482,181 B1 | 11/2002 | Racenet et al. | |
| 6,544,210 B1 | 4/2003 | Trudel et al. | |
| 6,551,283 B1 | 4/2003 | Guo et al. | |
| 6,569,120 B1 | 5/2003 | Green et al. | |
| 6,602,240 B2 | 8/2003 | Hermann et al. | |
| 6,610,031 B1 | 8/2003 | Chin | |
| 6,663,598 B1 | 12/2003 | Carrillo, Jr. et al. | |
| 6,685,665 B2 | 2/2004 | Booth et al. | |
| 6,702,787 B2 | 3/2004 | Racenet et al. | |
| 6,712,791 B2 | 3/2004 | Lui et al. | |
| 7,052,454 B2 | 5/2006 | Taylor | |
| 7,153,261 B2 | 12/2006 | Wenchell | |
| 7,163,510 B2 | 1/2007 | Kahle et al. | |
| 7,235,062 B2 | 6/2007 | Brustad | |
| 7,244,244 B2 | 7/2007 | Racenet et al. | |
| 7,390,317 B2 | 6/2008 | Taylor et al. | |
| 7,473,221 B2 | 1/2009 | Ewers et al. | |
| 7,481,765 B2 | 1/2009 | Ewers et al. | |
| 8,585,632 B2 | 11/2013 | Okoniewski | |
| 8,932,249 B2 | 1/2015 | Parihar et al. | |
| 9,022,986 B2 | 5/2015 | Gresham | |
| 10,874,426 B2 * | 12/2020 | Holsten | .............. A61B 17/3474 |
| 2001/0041871 A1 | 11/2001 | Brimhall | |
| 2001/0049499 A1 | 12/2001 | Lui et al. | |
| 2001/0049508 A1 | 12/2001 | Fangrow, Jr. et al. | |
| 2002/0013552 A1 | 1/2002 | Dennis | |
| 2002/0100262 A1 * | 8/2002 | Gieseke | .............. B01D 46/527 |
| | | | 55/385.3 |
| 2002/0128603 A1 * | 9/2002 | Booth | ................ A61B 17/3421 |
| | | | 604/164.01 |
| 2003/0032858 A1 | 2/2003 | Ginn et al. | |
| 2003/0040711 A1 | 2/2003 | Racenet et al. | |
| 2003/0050604 A1 | 3/2003 | Lui et al. | |
| 2003/0139756 A1 | 7/2003 | Brustad | |
| 2003/0195472 A1 | 10/2003 | Green et al. | |
| 2003/0208104 A1 | 11/2003 | Carrillo, Jr. et al. | |
| 2004/0015185 A1 | 1/2004 | Ewers et al. | |
| 2004/0054353 A1 | 3/2004 | Taylor | |
| 2004/0059297 A1 | 3/2004 | Racenet et al. | |
| 2004/0066008 A1 | 4/2004 | Smith | |
| 2004/0093018 A1 | 5/2004 | Johnson | |
| 2004/0106942 A1 | 6/2004 | Taylor et al. | |
| 2004/0111060 A1 | 6/2004 | Racenet et al. | |
| 2004/0254426 A1 | 12/2004 | Wenchell | |
| 2005/0020884 A1 | 1/2005 | Hart et al. | |
| 2005/0059934 A1 | 3/2005 | Wenchell et al. | |
| 2005/0096605 A1 | 5/2005 | Green et al. | |
| 2005/0096695 A1 | 5/2005 | Olich | |
| 2005/0148823 A1 | 7/2005 | Vaugh et al. | |
| 2005/0165433 A1 | 7/2005 | Haberland et al. | |
| 2005/0212221 A1 | 9/2005 | Smith et al. | |
| 2005/0267419 A1 | 12/2005 | Smith | |
| 2006/0041232 A1 | 2/2006 | Stearns et al. | |
| 2006/0047284 A1 | 3/2006 | Gresham | |
| 2006/0047293 A1 | 3/2006 | Jaberland et al. | |
| 2006/0084842 A1 | 4/2006 | Hart et al. | |
| 2006/0129165 A1 | 6/2006 | Edoga et al. | |
| 2006/0149305 A1 | 7/2006 | Cuevas et al. | |
| 2006/0224120 A1 | 10/2006 | Smith et al. | |
| 2006/0264991 A1 | 11/2006 | Johnson et al. | |
| 2006/0276751 A1 | 12/2006 | Haberland et al. | |
| 2007/0055107 A1 | 3/2007 | Wenchell | |
| 2007/0088241 A1 | 4/2007 | Brustad et al. | |
| 2007/0088274 A1 | 4/2007 | Stubbs et al. | |
| 2007/0116854 A1 | 5/2007 | Taylor et al. | |
| 2007/0151566 A1 | 7/2007 | Kahle et al. | |
| 2007/0197972 A1 | 8/2007 | Racenet et al. | |
| 2007/0233006 A1 | 10/2007 | Brustad | |
| 2008/0011307 A1 | 1/2008 | Beckman et al. | |
| 2008/0033363 A1 | 2/2008 | Haberland et al. | |
| 2008/0077169 A1 | 3/2008 | Taylor et al. | |

(56) References Cited

U.S. PATENT DOCUMENTS

| | | |
|---|---|---|
| 2008/0086074 A1 | 4/2008 | Taylor et al. |
| 2009/0048683 A1 | 2/2009 | Morris et al. |
| 2009/0076465 A1 | 3/2009 | Berry et al. |
| 2010/0004599 A1 | 1/2010 | Zhou et al. |
| 2010/0241061 A1 | 9/2010 | Ott |
| 2011/0308524 A1* | 12/2011 | Brey ............. A62B 23/02 128/205.12 |
| 2012/0165610 A1 | 6/2012 | Poll |
| 2016/0106952 A1 | 4/2016 | Mastri et al. |
| 2016/0158468 A1 | 6/2016 | Tang et al. |

FOREIGN PATENT DOCUMENTS

| | | |
|---|---|---|
| DE | 3217118 C1 | 8/1983 |
| DE | 3737121 A1 | 5/1989 |
| DE | 202008009527 U1 | 10/2008 |
| EP | 0051718 A1 | 5/1982 |
| EP | 0113520 A2 | 7/1984 |
| EP | 0169787 A1 | 1/1986 |
| EP | 0312219 A2 | 4/1989 |
| EP | 0538060 A1 | 4/1993 |
| EP | 1188415 A2 | 3/2002 |
| EP | 1629787 A2 | 3/2006 |
| EP | 1698291 A1 | 9/2006 |
| GB | 1482857 A | 8/1977 |
| JP | 50112652 | 9/1975 |
| JP | 58163867 | 9/1983 |
| JP | 06061518 | 4/1994 |
| JP | 07241298 | 9/1995 |
| JP | 2002204829 A | 7/2002 |
| JP | 2007508061 A | 4/2007 |
| JP | 5103854 B2 | 12/2012 |
| KR | 100851844 B1 | 8/2008 |
| KR | 101731472 B1 | 5/2017 |
| NO | 9513313 A1 | 5/1995 |
| WO | 9304717 A1 | 3/1993 |
| WO | 9417844 A1 | 8/1994 |
| WO | 9853865 A1 | 12/1998 |
| WO | 02087682 A2 | 11/2002 |
| WO | 03011154 A2 | 2/2003 |
| WO | 2004043275 A1 | 5/2004 |
| WO | 2007119232 A2 | 10/2007 |

OTHER PUBLICATIONS

Korean Office Action dated Jan. 4, 2023, issued in corresponding Korean Application No. 10-2018-0015353, 2 pages.
Japanese Office Action dated Oct. 21, 2021 for application No. 2018-020016.
European Search Report issued in European Application No. EP 18155923.8 dated Apr. 5, 2018.

* cited by examiner

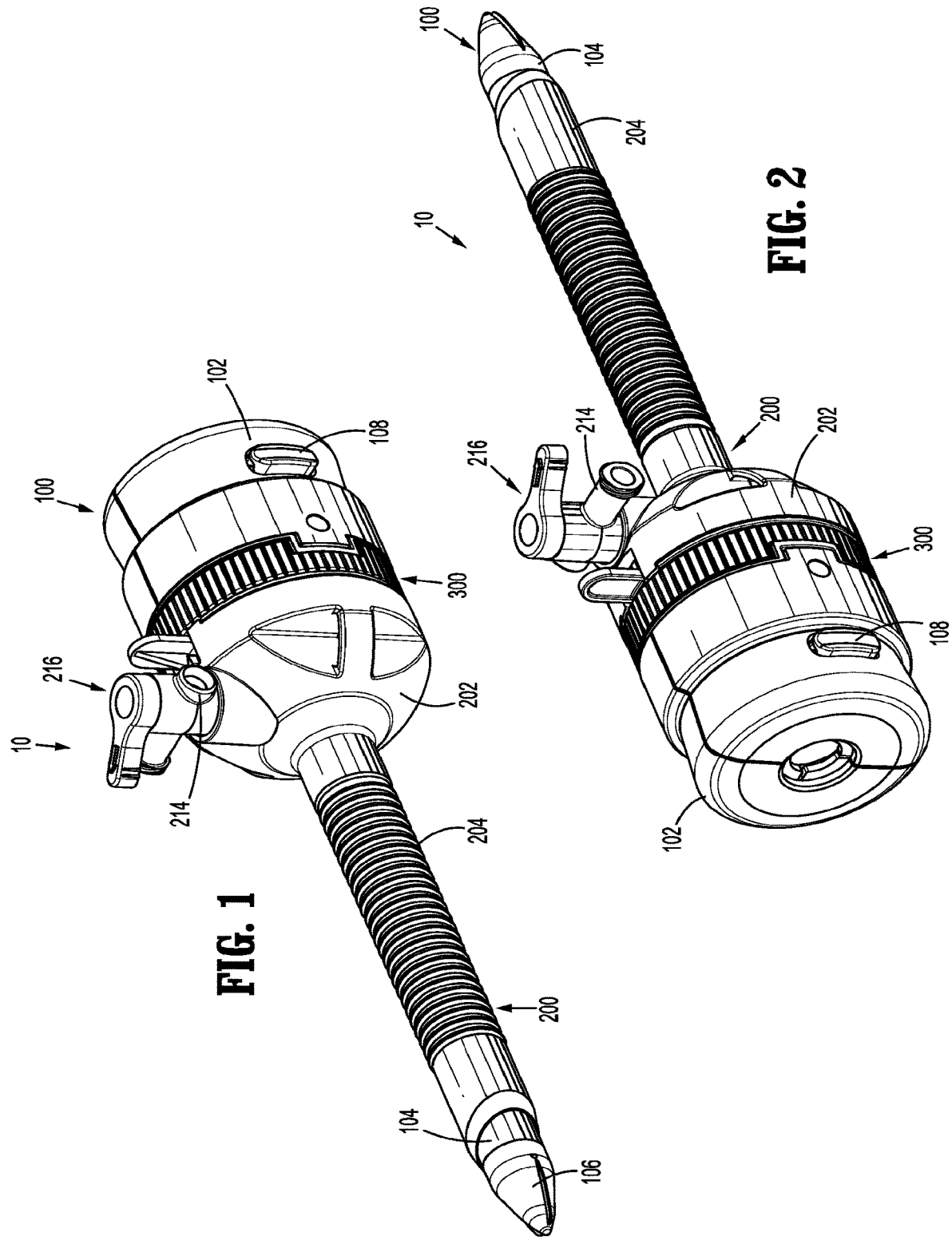

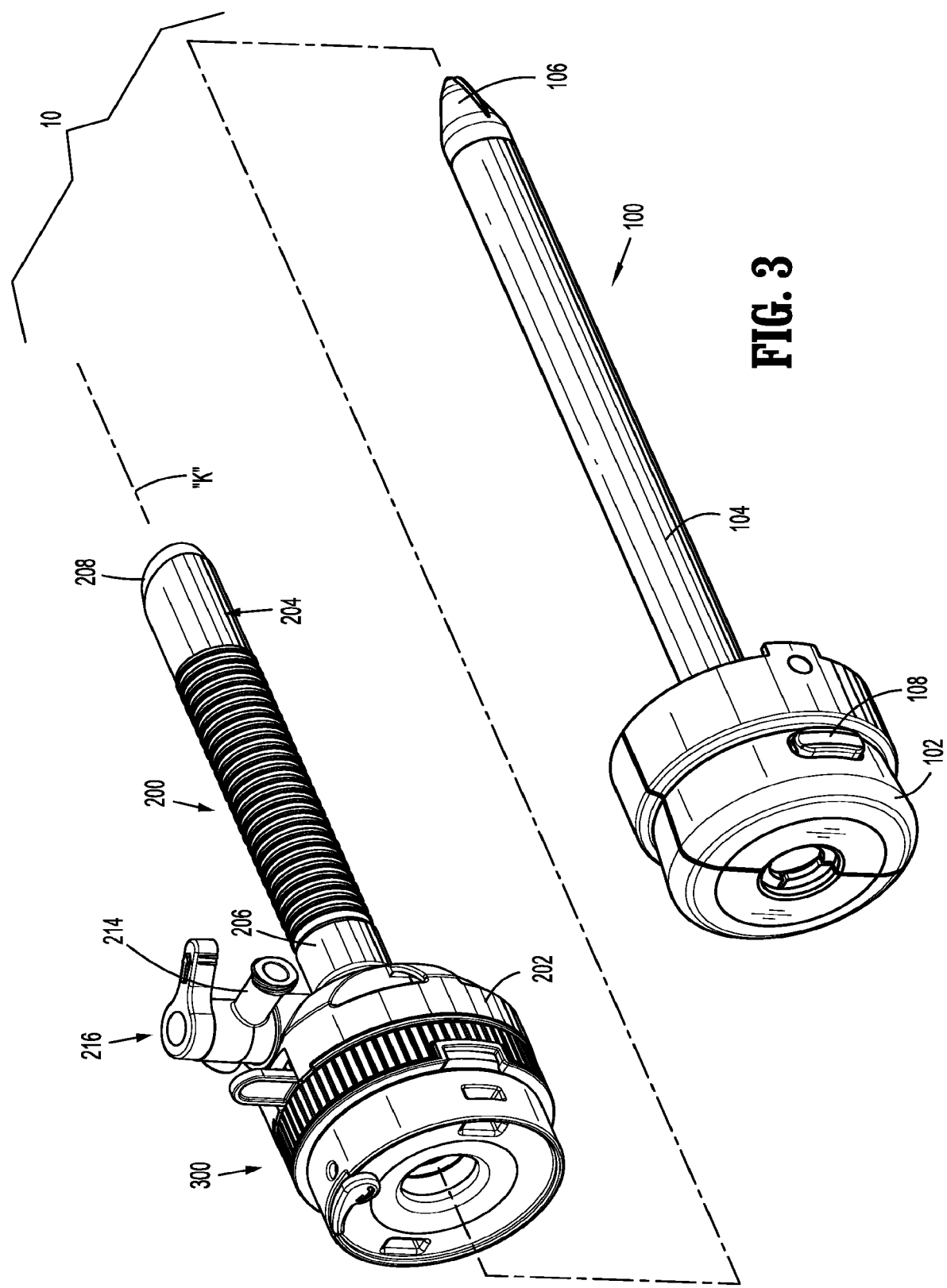

SEAL ASSEMBLY WITH INTEGRAL FILTER AND EVACUATION PORT

CROSS-REFERENCE TO RELATED APPLICATIONS

This application is a continuation of U.S. patent application Ser. No. 15/876,699, filed Jan. 22, 2018, which claims the benefit of and priority to U.S. Provisional Patent Application Ser. No. 62/457,511, filed Feb. 10, 2017, and U.S. Provisional Patent Application Ser. No. 62/573,308, filed Oct. 17, 2017, the contents of each of which are incorporated by reference herein.

BACKGROUND

1. Technical Field

The present disclosure relates to an access apparatus for accessing a body cavity. More particularly, the present disclosure relates to an assembly for use with an access apparatus and having a filter for filtering and evacuating smoke and other contaminants generated during performance of a surgical procedure.

2. Background of Related Art

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the instrument to preserve the integrity of the pneumoperitoneum.

Instruments utilized during a laparoscopic procedure may include lasers, electro-cautery or sonic cutting instruments, which produce smoke and/or an aerosol as a byproduct of treating tissue. Smoke plumes can obscure the clinician's field of vision and the odor generated is unpleasant. Further, the smoke plume may contain infectious agents which may contaminate the operating arena thereby presenting a danger to operating personnel. Chemical vapor may be irritating to the respiratory tract and also may be carcinogenic. The smoke, noxious fumes, and other gases and vapors can include particulates, bacteria, viral elements and undesirable odors.

Conventional methodologies for evacuating smoke include using a surgical smoke evacuation device. This device includes a vacuum pump, tubing, and a filter to filter out particulates and microbials and properly dispose of them. A tube is typically attached to the insufflation port of an access cannula and the smoke is ventilated through the filter. However, this arrangement interrupts the surgical procedure requiring the additional steps of disconnecting the insufflation port from the gas source, mounting the filter to the insufflation port and thereafter reconnecting the gas source to reestablish the pneumoperitoneum to continue the surgical procedure. The separate filter also adds an additional component and expense thereby increasing the cost of the underlying procedure.

Removing the smoke, gases and vapors is typically done through a mechanical filtration method. Because the surgical field is a high moisture environment, the filter tends to clog. The clogged filter and reduced flow rate becomes a limiting factor. Also, it is desirable not to disadvantageously impact pneumoperitoneum.

It would be desirable to provide smoke evacuation during surgery in a compact, efficient arrangement that can also reduce cost.

SUMMARY

Accordingly, the present disclosure is directed to a seal assembly for use with an access apparatus to provide filtering of fluids, e.g., smoke, from an operating site and to remove contaminants and/or odor from the fluids for release of the filtered fluids into the ambient atmosphere. The seal assembly may be a separate subassembly or component which is releasably couplable to the access apparatus or may be integral with the access apparatus. In accordance with an embodiment, a seal assembly for use with a cannula assembly is disclosed. The cannula assembly may be of the type including a cannula housing and a cannula sleeve extending from the cannula housing. The cannula sleeve is configured for accessing an underlying body cavity and defines a longitudinal passage for introduction of a surgical object. The seal assembly includes a seal housing couple-able to the cannula housing of the cannula assembly and defining a seal axis, and having an axial opening there through for passage of a surgical object. The seal housing includes an evacuation port. An object seal is mounted to the seal housing for sealed reception of the surgical object. The object seal and the seal housing are configured to define a flow path communicating with the longitudinal passage of the cannula sleeve and extending proximal of the object seal to permit passage of fluids from the underlying body cavity to exit the evacuation port. A filter is mounted to the seal housing and configured for filtering smoke and/or contaminants from the fluids. An evacuation valve is mounted to the seal housing adjacent the filter. The evacuation valve is selectively transitionable between a closed position and an open position to respectively close and open the evacuation port.

In an embodiment, the filter is disposed proximal of the object seal. In certain embodiments, the seal housing includes a distal housing component having an internal seal mount disposed distal of the object seal and configured for supporting the object seal. The internal seal mount defines at least one flow channel configured to permit passage of fluids about a peripheral segment of the object seal. The at least one flow channel is a component of the flow path. In some embodiments, the internal seal mount defines a plurality of flow channels radially spaced relative to the seal axis.

In certain embodiments, the seal housing includes an intermediate housing component configured for at least partially enclosing the object seal. The intermediate housing component defines a plurality of flow openings in fluid communication with the flow channels of the internal seal mount to permit passage of fluids proximal of the intermediate housing component. The plurality of flow openings is a component of the flow path.

In embodiments, the filter is disposed adjacent the intermediate housing component and is in fluid communication with the flow openings of the intermediate housing component. The filter is a component of the flow path.

In some embodiments, the seal housing includes a proximal housing component for at least partially accommodating the filter. The proximal housing component has the evacuation port defined in a side wall thereof with the evacuation port being a component of the flow path.

In embodiments, the filter comprises a high-density polyethylene material (HDPE) with or without activated charcoal. In some embodiments, the filter is pleated and may have straight or curved pleats. In certain embodiments, the filter comprises polyurethane with activated charcoal. In embodiments, the filter is an ultra-low particulate air (ULPA) filter with or without activated charcoal. In other embodiments, it may include a high efficiency particulate air, or HEPA, filter.

In accordance with another aspect of the present disclosure, a surgical cannula assembly comprises a seal housing and at least one seal for providing a seal around a surgical instrument, the cannula assembly has a cannula and a filter in a flow path extending proximally from a distal end of the cannula. The filter allows up to 10 liters of small particulate air flow per minute and has about 3 to about 10 square inches of combined surface area. However, the filter may allow greater than 3 liters of small particulate air flow per minute, or more than 10 liters of small particulate air flow per minute.

In further examples, the filter has an activated carbon element and an ultra-low particulate air filter element. The filter can be incorporated in a filter housing attachable to the seal housing. The filter can be disposed in the seal housing. The filter may be disposed in the seal housing, proximal to the seal, or proximal to the zero closure seal, or elsewhere on the cannula assembly. The filter includes can have an activated carbon material in a layer.

The filter, in further examples, includes an ultra-low particulate air filter element and the activated carbon material. The filter can include an ultra-low particulate air filter element defining a plurality of pleats. The pleats can be one of radially oriented and vertically oriented. The filter can include an ultra-low particulate air filter element defining a plurality of tubular elements. The filter can include an ultra-low particulate air filter element defining a plurality of layers.

In further examples, the filter includes a plurality of layers of activated carbon material.

In a further aspect of the present disclosure, a seal assembly for use with a surgical cannula assembly comprises: a seal housing defining a seal axis, the seal housing defining an axial opening therethrough for passage of a surgical object and having an evacuation port; a filter in the seal housing configured for filtering smoke and/or contaminants from the fluids, the filter having a filter material; and an evacuation valve on the seal housing and adjacent the filter, the evacuation valve selectively transitionable between a closed position and an open position to respectively close and open the evacuation port.

In the seal assembly according to the present example, the filter material defines multiple turns. The filter material can also define multiple pleats. The filter material can define multiple layers. The filter material can define multiple tubular elements.

The seal assembly can further include an object seal in the seal housing for sealed reception of the surgical object. The object seal and the seal housing can be configured to define a flow path communicating with the longitudinal passage of the cannula sleeve and extending proximal of the object seal to permit passage of fluids from the underlying body cavity to exit the evacuation port.

The filter can be disposed proximal of the object seal. The seal housing can define at least one flow channel configured to permit passage of fluids about a peripheral segment of the object seal. The seal housing can define a plurality of flow channels radially spaced relative to the seal axis.

The seal housing can include an intermediate housing component configured for at least partially enclosing the object seal; the intermediate housing component can define a plurality of flow openings in fluid communication with the flow channels of the internal seal mount to permit passage of fluids proximal of the intermediate housing component. The filter can be disposed adjacent the intermediate housing component, the filter being in fluid communication with the flow openings of the intermediate housing component.

The seal housing can include a proximal housing component for at least partially accommodating the filter; the proximal housing component can have the evacuation port. The filter can comprise an ultra-low particulate air filter material and activated carbon. The filter can comprise polyurethane with activated carbon.

In a further aspect, a cannula assembly comprises a cannula housing and a cannula member extending from the cannula housing and defining a longitudinal cannula axis. The cannula member has proximal and distal ends. The cannula housing and the cannula member have a longitudinal opening for reception of a surgical object and the cannula member is configured to access an underlying body cavity. An insufflation port is in the cannula housing for passage of insufflation gases, and a seal housing is couplable to the cannula housing and defines a seal axis in general alignment with the longitudinal cannula axis The seal housing defines an axial opening therethrough for passage of the surgical object, the seal housing defines an evacuation port proximal of the insufflation port. An object seal is in the seal housing for sealed reception of the surgical object, the object seal and the seal housing defining a flow path communicating with the longitudinal opening of the cannula housing and the cannula sleeve and extending proximal of the object seal to permit passage of fluids from the underlying body cavity through the longitudinal opening to exit the evacuation port of the seal housing. A filter is in the seal housing for filtering at least one of smoke and contaminants from the fluids. An evacuation valve is mounted to the seal housing adjacent the filter, the evacuation valve selectively transitionable between a closed position and an open position to respectively close and open the evacuation port.

In further examples, an insufflation valve is in fluid communication with the insufflation port of the cannula housing to selectively open and close the insufflation port, the insufflation valve independent of the evacuation valve. The filter can be disposed proximal of the object seal. An obturator assembly can be included, the obturator assembly having a shaft defining a passageway and a distal end defining a tip, the tip having an opening adjacent the distal end. The obturator assembly can have a handle at a proximal end thereof, the handle having an opening communicating with the passageway. A luer can be included. The access assembly can include a movable top positionable over the opening of the handle, and the luer can be attached to the top.

A surgical access kit can comprise a surgical cannula assembly having a first seal housing and a cannula. The first seal housing can have an object seal therein, and a second seal housing can be included, with an object seal disposed therein and a filter element disposed in the second seal housing.

A surgical obturator can be included in the kit. The surgical obturator may be at least partially transparent. The surgical obturator can have a tapered, blunt tip. In further examples, the surgical obturator defines an insufflation pathway including an opening at a distal end. The surgical obturator can define an insufflation pathway including an opening at a distal end, the opening having a central axis that is angled about 60 degrees from a longitudinal axis of the obturator.

Other advantages of the seal assembly with integral filter and evacuation port will be appreciated from the following description.

BRIEF DESCRIPTION OF THE DRAWINGS

Various aspects and features of the present disclosure are described hereinbelow with references to the drawings, wherein:

FIGS. 1-2 are perspective views of a seal assembly of the present disclosure mounted to a surgical trocar apparatus including an obturator assembly and a cannula assembly;

FIG. 3 is an exploded perspective view illustrating the obturator assembly removed with the seal assembly mounted to the cannula assembly;

DETAILED DESCRIPTION

Figure 4:
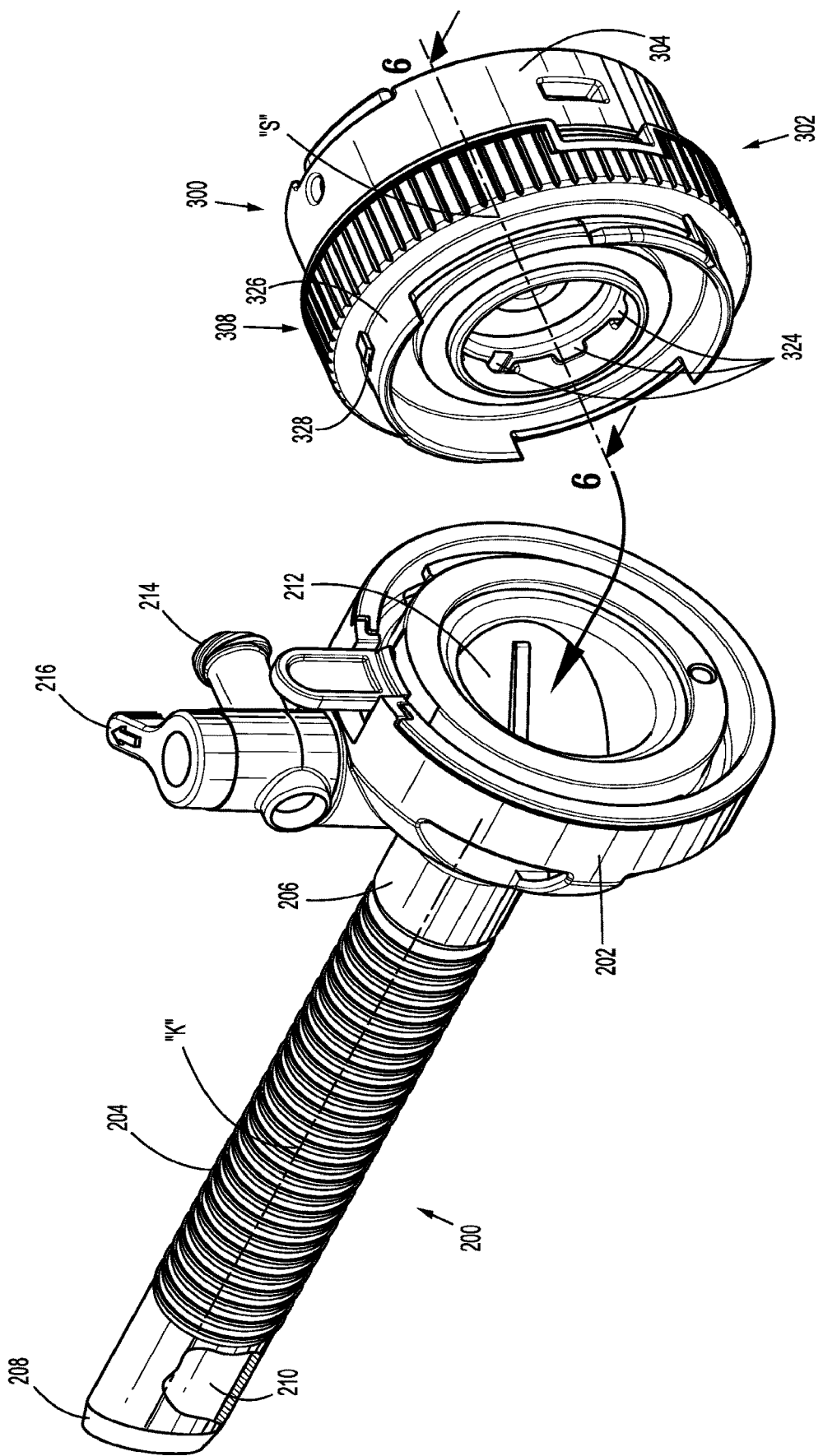
FIG. 4 is a perspective view illustrating the seal assembly removed from the cannula assembly.

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

The present disclosure relates to a seal assembly which may be incorporated with an access apparatus, such as a cannula assembly, for the removal and/or treatment of fluids from, e.g., the peritoneal cavity, during a laparoscopic procedure. Such fluids may include smoke and other gaseous material in addition to aerosol and particle byproducts of the laparoscopic procedure involving cutting, heating or burning, and may include, for example, chemicals, ultrasonic vapors, particles, and ion dust particles. More particularly, the present disclosure relates to a seal assembly having a filter and evacuation port that efficiently removes smoke, odor, vapor, particles or plumes released by chemicals or produced by the use of lasers, sonic cutting and/or cautery or other surgical techniques or instruments, (hereinafter, collectively referred to as "contaminated fluids"), from within the peritoneal cavity.

The following discussion will focus on the use of the seal assembly with a trocar apparatus having an obturator assembly positionable within a cannula assembly. However, the seal assembly may be utilized in other capacities such as, e.g., in hand access systems where the surgeon's hand is introduced within the peritoneal cavity to assist in performing the laparoscopic procedure. The seal assembly may be contemplated for use in surgical procedures in other areas of the body, e.g., in other endoscopic procedures including arthroscopic, gynecological, spinal procedures, and the like.

Referring initially to FIGS. 1-3, there is illustrated an access assembly incorporating the seal assembly of the present disclosure. The access assembly is intended to permit access to an insufflated peritoneal cavity during a laparoscopic procedure to permit the introduction of a surgical object for performing various surgical tasks on internal organs within the cavity. The surgical object may be a surgical instrument such as laparoscopic or endoscopic clip appliers, graspers, dissectors, retractors, staplers, laser probes, photographic devices, tubes, endoscopes and laparoscopes, electro-surgical devices, and the like.

In one embodiment, the access apparatus is in the form of a trocar apparatus 10 which includes an obturator assembly 100, a cannula assembly 200 for at least partial reception of the obturator assembly 100 and a seal assembly 300 which is selectively mountable to the cannula assembly 200 to provide sealing capabilities, e.g., to establish a sealing relation about an inserted surgical object. In general, the obturator assembly 100 includes an obturator handle 102 and an elongated obturator member 104 extending from the obturator handle 102. The obturator member 104 typically includes a penetrating end 106 for passage through tissue. In some embodiments, the penetrating end 106 is closed and transparent to permit visualization during entry of the trocar apparatus 10 within an insufflated body cavity such as the peritoneal cavity, e.g., with an endoscope introduced through the obturator assembly 100. The obturator assembly 100 may include a mechanism to permit selective coupling with either or both the cannula assembly 200 and with the seal assembly 300 such as a pair of latches 108 which engage corresponding structure of the assemblies 200, 300.

With reference to FIG. 4, in conjunction with FIGS. 1-3, the cannula assembly 200 includes a cannula housing 202 and a cannula sleeve 204 extending from the cannula housing 202. The cannula sleeve 204 defines proximal and distal ends 206, 208 and a longitudinal axis "k" extending along the length of the cannula sleeve 204. The cannula housing 202 and the cannula sleeve 204 define a longitudinal opening 210 (cut-away in FIG. 4) for reception and passage of the surgical object. The cannula housing 202 may include a zero closure valve 212, e.g., a duckbill valve, which is configured to close in the absence of a surgical object to prevent egress of insufflation gases. The zero closure valve 212 does not typically establish a seal about an inserted surgical object. The cannula housing 202 also includes an insufflation port 214 and associated insufflation valve 216 (e.g., a stop cock valve) for selective introduction of insufflation fluids into the cannula sleeve 204 and the peritoneal cavity. Further details of an obturator assembly 100 and cannula assembly 200 for use with the seal assembly 300 may be ascertained by reference to commonly assigned U.S. Publication No. 2015-0216560 to Holsten, the entire contents of which is hereby incorporated by reference herein.

Figure 5:
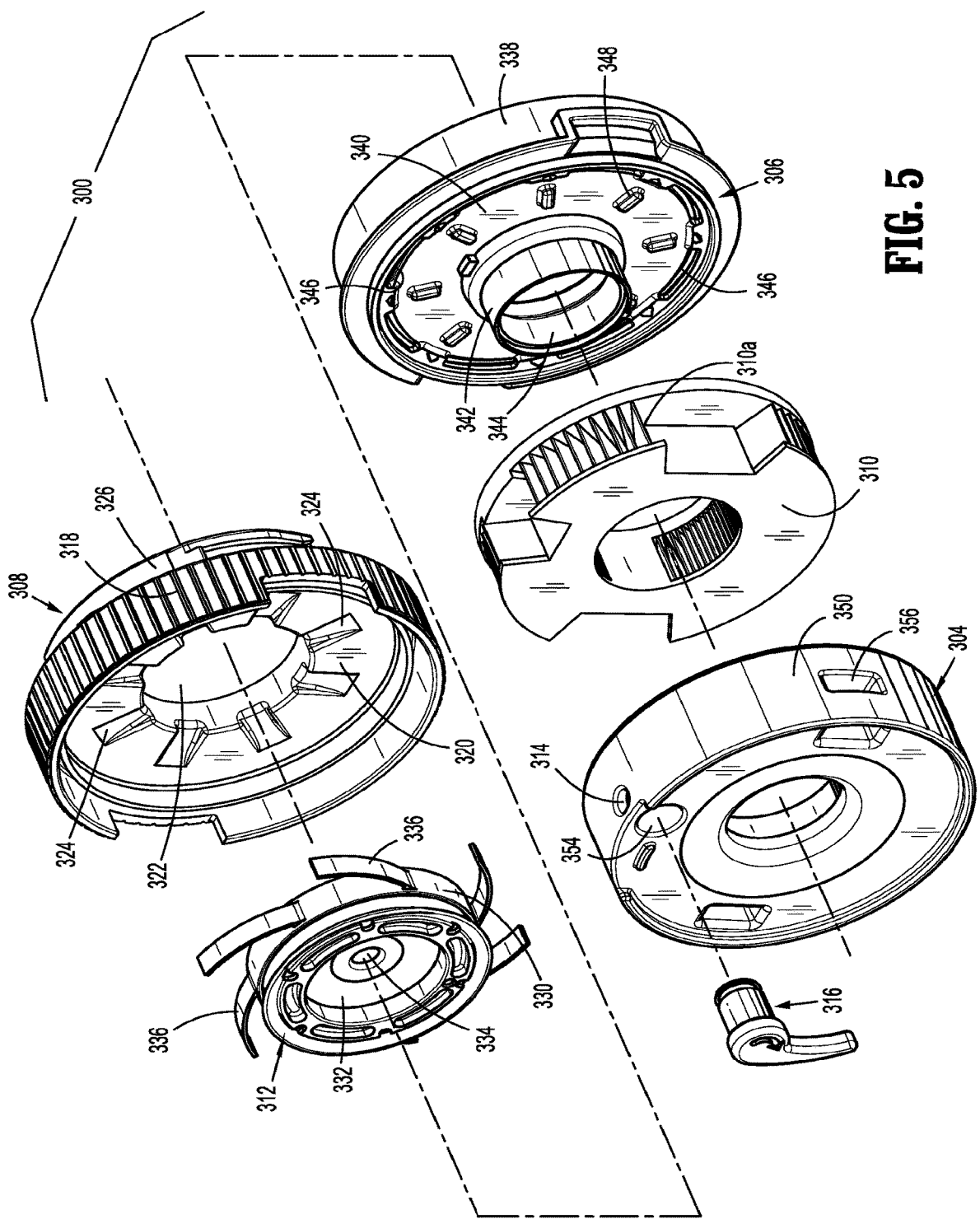
FIG. 5 is an exploded perspective view of the seal assembly illustrating the proximal housing component with evacuation valve, the filter, the intermediate housing component, the object seal and the distal housing component.
Figure 6:
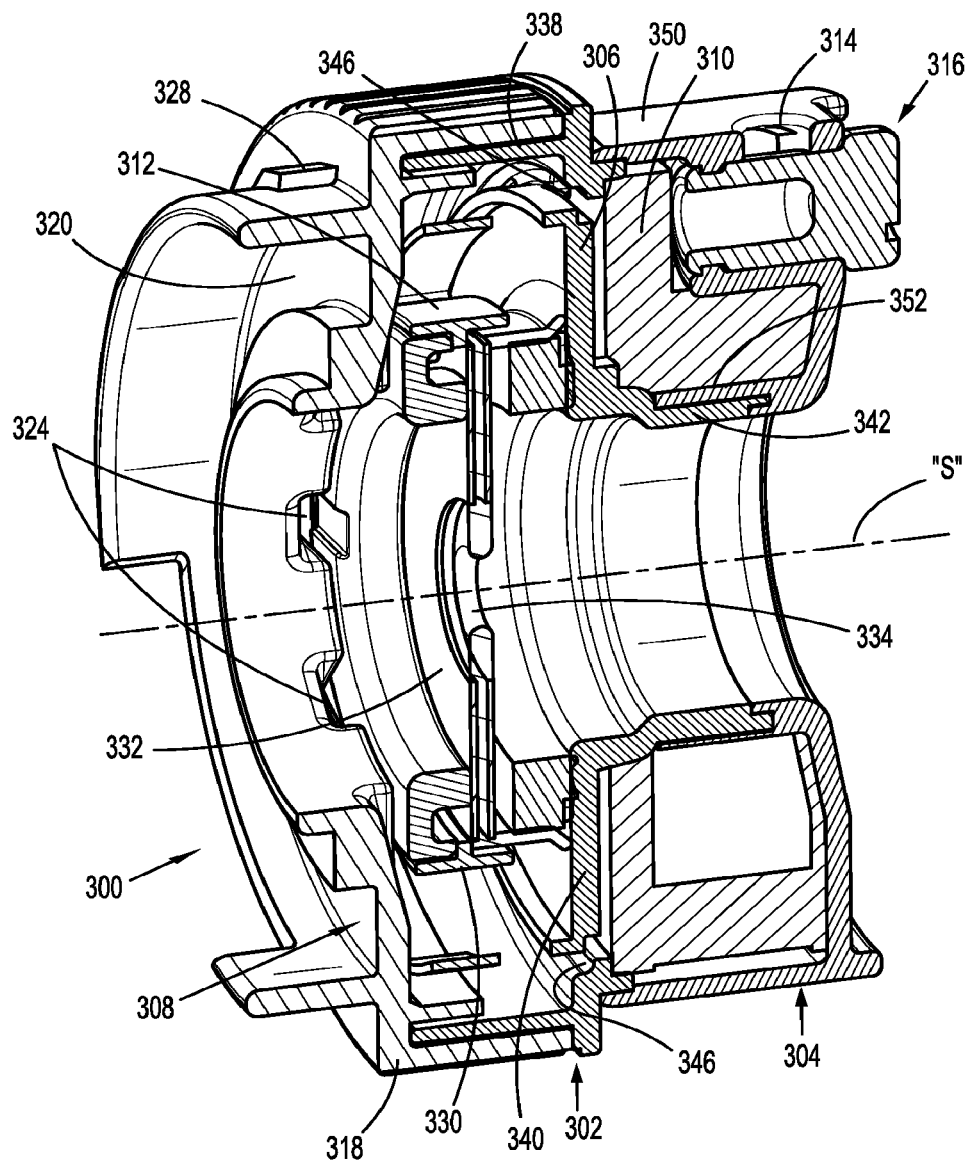
FIG. 6 is a cross-sectional view of the seal assembly taken along the lines 6-6 of FIG. 4.

Referring now to FIGS. 4-6, the seal assembly 300 will be discussed. The seal assembly 300 is selectively, e.g., releasably, couplable to the cannula housing 202 of the cannula assembly 200 to provide sealing capabilities about an inserted surgical object. Any mechanism for releasably mounting the seal assembly 300 to the cannula housing 202 is envisioned including, e.g., a friction fit, bayonet coupling, snap fit, and the like. The seal assembly 300 includes a seal housing, identified generally as reference numeral 302, defining a seal axis "s" (FIG. 6) which is in general longitudinal alignment with the longitudinal axis "k" of the cannula sleeve 204 in the assembled condition of the components. The seal housing 302 may include a number of assembled components including, from proximal to distal, a proximal housing component 304, an intermediate housing component 306 and a distal housing component 308. In the alternative, the seal housing 302 may be a single component monolithically or integrally formed to incorporate the proximal, intermediate and distal housing components 304, 306, 308.

As best depicted in FIGS. 5-6, the seal assembly 300 further includes a filter 310 disposed between the proximal and intermediate housing components 304, 306 and an object seal 312 disposed between the intermediate and distal housing components 306, 308. The filter 310 may be disposed proximal of the object seal 312. The seal assembly 300 also includes an evacuation port 314 in the proximal housing component 304 and an evacuation valve 316 adjacent the evacuation port 314 for selective release of the fluids from the peritoneal cavity. In other examples, the filter can be proximal the zero closure (duckbill) seal, or located elsewhere on the cannula assembly.

Figure 7:
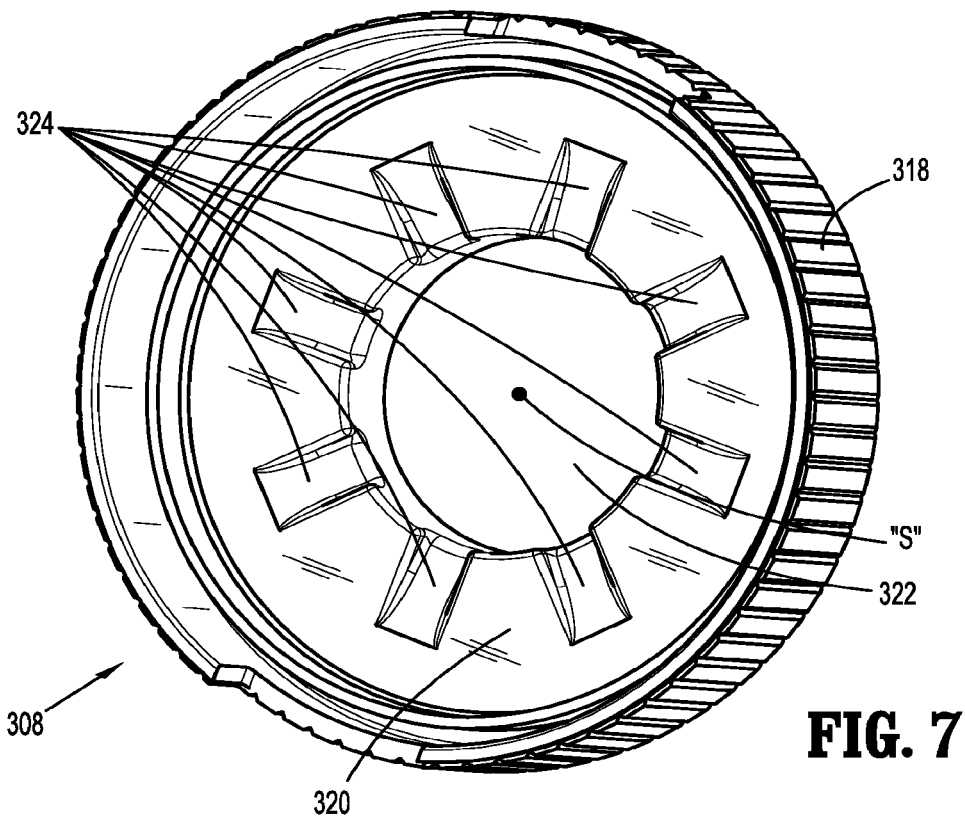
FIG. 7 is a perspective view illustrating the distal housing component of the seal assembly.

Referring now to FIGS. 5-7, the distal housing component 308 of the seal assembly will be discussed. The distal housing component 308 is directly couplable to the cannula housing 202 through any of the aforementioned mechanisms. The distal housing component 308 includes a distal housing collar 318, an internal seal mount 320 depending radially inwardly from the distal housing collar 318 and a central mount aperture 322 in general alignment with the seal axis "s". The outer surface of the distal housing collar 318 may include roughened surfaces, e.g., ribs, scallops, and the like, to facilitate engagement and manipulation by the user. The internal seal mount 320 includes at least one or more flow channels 324 extending radially outward from the central mount aperture 322 toward the distal housing collar 318. In embodiments, a plurality of flow channels 324 are defined in the internal seal mount 320 and may be radially and equidistally spaced relative to the seal axis "s". The flow channels 324 permit passage of fluids about or around the perimeter of the object seal 312 for conveyance toward the evacuation port 314. The flow channels 324 are formed in the proximal face of the internal seal mount 320 and may be coterminous with the central mount aperture 322. In embodiments, the internal seal mount 320 tapers upwardly toward the distal housing collar 318 such that the flow channels 324 define a depth which is greatest adjacent the central mount aperture 322 and decreases toward the distal housing collar 318. This resultant taper of the flow channels 324 assists in directing the fluids proximally toward the evacuation port 314.

The distal housing collar 318 of the distal housing component 308 also includes a mounting collar 326 (FIG. 5) which is at least partially positionable within the cannula housing 202. The mounting collar 326 may include one or more fingers 328 (FIGS. 4 and 6) to assist in coupling the distal housing component 308 to the cannula housing 202. Further details of an exemplary coupling mechanism may be ascertained by reference to the '359 application previously incorporated by reference herein.

Referring again to FIGS. 5 and 6, the object seal 312 includes an outer seal collar 330 and a seal member 332 depending radially inwardly from the seal collar 330. The seal member 332 may be fabricated, at least in part, from an elastomeric material with one or more fabric layers positioned on, or embedded within, the elastomeric material. The seal member 332 defines a seal passage 334 for reception and passage of a surgical object in sealed relation therewith. The upper and lower portions of the seal collar 330 form a seal with the housing component. A plurality of resilient spokes 336 depends outwardly from the seal collar 330. The spokes 336 bias the seal member 332 to a position where the seal passage 334 is in general alignment with the seal axis "s", and may minimize offset movement of the seal member 334 during manipulation of the surgical object. Other resilient structures can be used for the same purpose. The seal member can have a flat, circular shape, a conical shape, or hemispherical.

Figure 8:
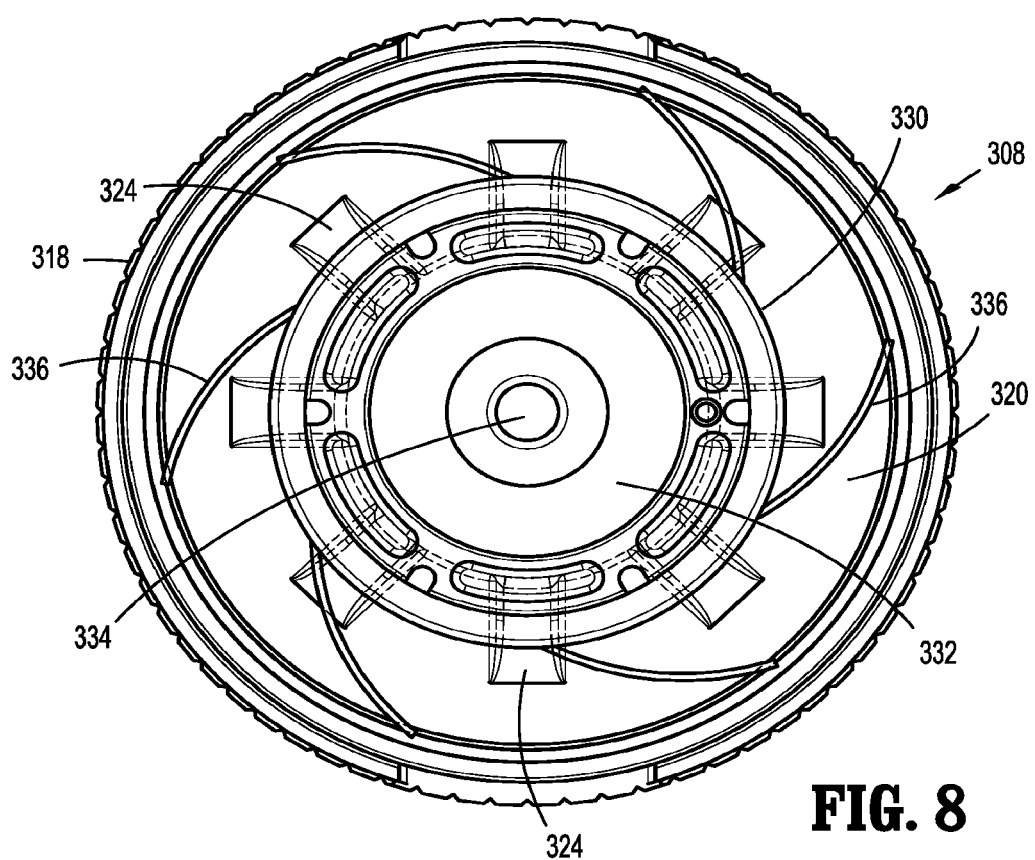
FIG. 8 is a top plan view illustrating the object seal mounted relative to the distal housing component.

As best depicted in FIG. 8, when positioned adjacent the internal seal mount 320 of the distal housing component 308, the seal collar 330 is generally disposed within the confines of the flow channels 324, i.e., the flow channels 324 extend radially outward of the seal collar 330. This arrangement ensures that the flow channels 324 are not blocked by the seal collar 330 thereby permitting the passage of fluids through the flow channels 324 and toward the evacuation port 314. FIG. 8 also depicts the spokes 336 engaging the distal housing collar 318 to assist in maintaining alignment of the seal passage 334 with the seal axis "s".

Figure 9:
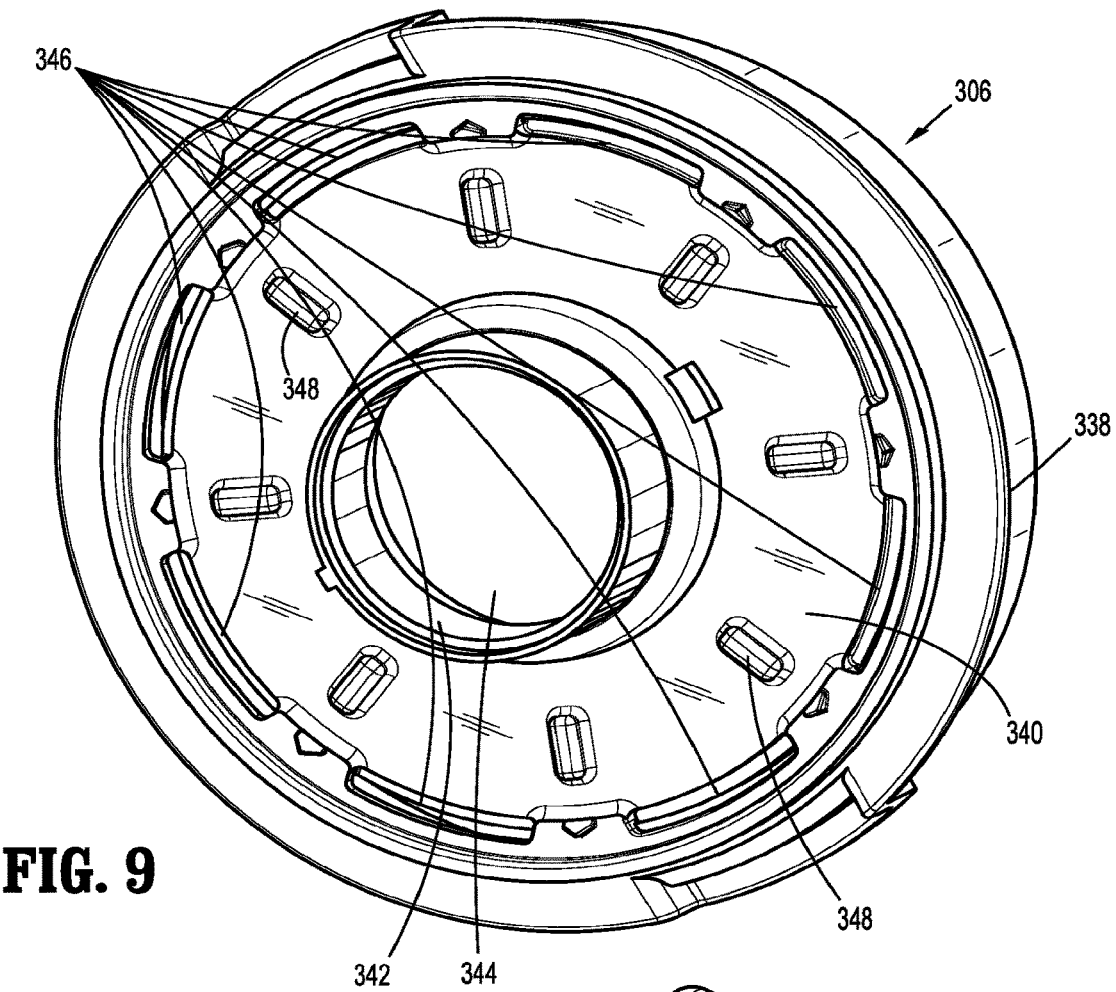
FIG. 9 is a perspective view of the intermediate housing component.

Referring now to FIG. 9, in conjunction with FIGS. 5 and 6, the intermediate housing component 306 includes an outer intermediate collar 338, a housing plate 340 depending inwardly from the outer intermediate collar 338 and a tube segment 342 contiguous with the housing plate 340 and defining an aperture 344 in alignment with the seal axis "s". The tube segment 342 extends in a proximal direction. The outer intermediate collar 338 is dimensioned for at least partial reception of the object seal 312, and is at least partially received within the distal housing collar 318 of the distal housing component 308 to trap the object seal 312 therebetween. The housing plate 340 defines a plurality of flow openings 346 disposed, e.g., at the intersection of the outer intermediate collar 338 and the housing plate 340. Other locations for the flow openings 346 are also envisioned. The flow openings 346 may be radially spaced relative to the seal axis "s", and, in some embodiments, are equidistally spaced. The flow openings 346 are in fluid communication with the flow channels 324 of the distal housing component 308 to permit flow of fluids toward the evacuation port 314. The proximal side of the housing plate 340 may include a plurality of spaced protuberances 348 which support the filter 310 in spaced relation to the housing plate 340 such that the filter 310 does not cover the flow openings 346.

With reference again to FIGS. 5-6, the filter 310 will be discussed. The filter 310 may be an ultra-high molecular filter 310 (or ULPA filter), activated carbon filter, a high efficiency particulate air filter (or HEPA filter) 310, or a combination of two or more of them. In an example, the filter 310 includes a high-density polyethylene material (HDPE) or a polyurethane material, with activated charcoal. In embodiments, the filter 310 includes linear or triangular pleats 310a. In embodiments, filter 310 is capable of providing a flow rate of at least 6 liters per minute (at 15 mm mercury) from the peritoneal cavity through the filter 310 and into the ambient environment. The filter 310 can be capable of removing smoke and contaminant particles from the fluid including nanoparticles or ultrafine particles of less than 0.12 microns in diameter with an efficiency rate of least 99.995%. These particles may be responsible for causing systemic diseases as a result of chronic exposure in operating rooms to health care personnel. Other filter arrangements are discussed hereinbelow. The filter 310 may be an ultra-low particulate air filter (ULPA filter) with or without carbon or other odor reducing elements. The filter 310 can include a combination of film, resins and/or activated carbon.

The filter can allow up to 10 liters of small particulate air flow. However, the filter may allow greater than 3 liters of small particulate air flow per minute, or more than 10 liters of small particulate air flow per minute.

Referring again to FIGS. 5 and 6, the proximal housing component 304 includes an outer proximal collar 350 and a central tube segment 352 (FIG. 6) depending longitudinally from the outer proximal collar 350. The central tube segment 352 couples with the tube segment 342 of the intermediate housing component 306. The spacing defined between the outer proximal collar 350 and the central tube segment 352 at least partially accommodates the filter 310. The outer proximal collar 350 further defines a longitudinal bore 354 (FIG. 5) offset relative to the seal axis "s" for at least partial reception of the evacuation valve 316. The longitudinal bore 354 is in fluid communication with the evacuation port 314. The evacuation port 314 extends through the sidewall of the outer proximal collar 350 orthogonal to the seal axis "s" to intersect the longitudinal bore 354. The proximal housing component 304 may be coupled to the intermediate housing component 306 by any of the aforementioned methodologies. The proximal housing component 304 also may include latch openings 356 for reception of the latches 108 of the obturator assembly 100.

The access assembly of FIGS. 1-16 has a filter incorporates into the seal housing for the cannula assembly. In other examples, a filter can be housed in its own housing and can be attached to the seal housing, and be separately provided. In further examples, the filter can be incorporated into, or attached to other parts of the cannula assembly. A filter assembly is provided in a flow path extending proximately from a distal end of the cannula, to filter out ultra small particulates, microbials, reduce moisture, etc.

Figure 10:
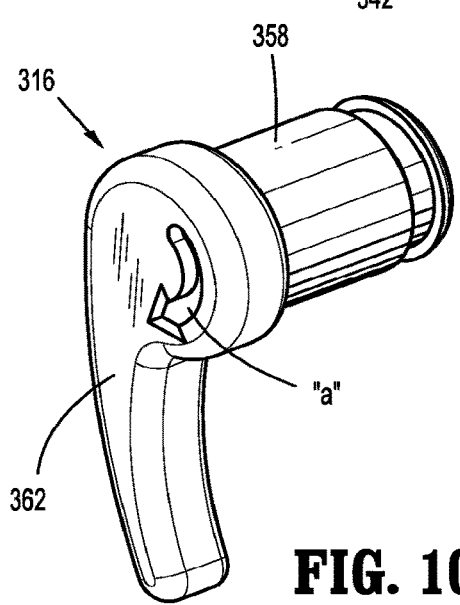
FIGS. 10-11 are perspective views of the evacuation valve.
Figure 11:
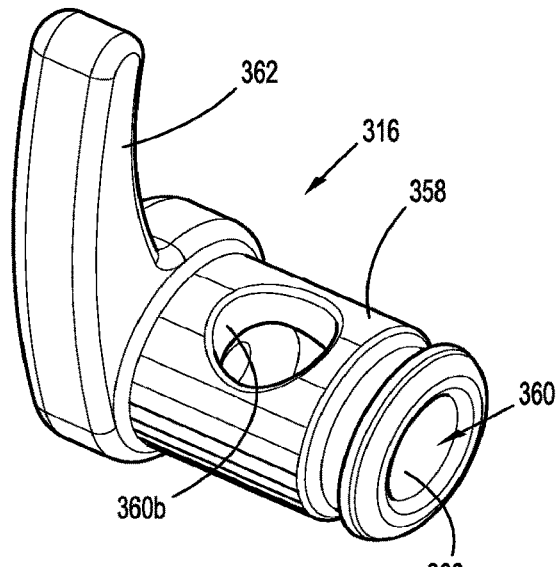

Referring now to FIGS. 10-11, the evacuation valve 316 will be discussed. The evacuation valve 316 includes a valve stem 358 defining a valve bore 360 having a longitudinal bore segment 360a and a radial bore segment 360b. The evacuation valve 316 further includes a manual member 362 coupled to the valve stem 358 for manual manipulation by the clinician. The manual member 362 may include visual indicia, e.g., in the form of a directional arrow "a", to assist the clinician in manipulation of the evacuation valve 316 from the closed position to the open position. The operation of the evacuation valve 316 will be discussed in greater detail hereinbelow.

Figure 12:
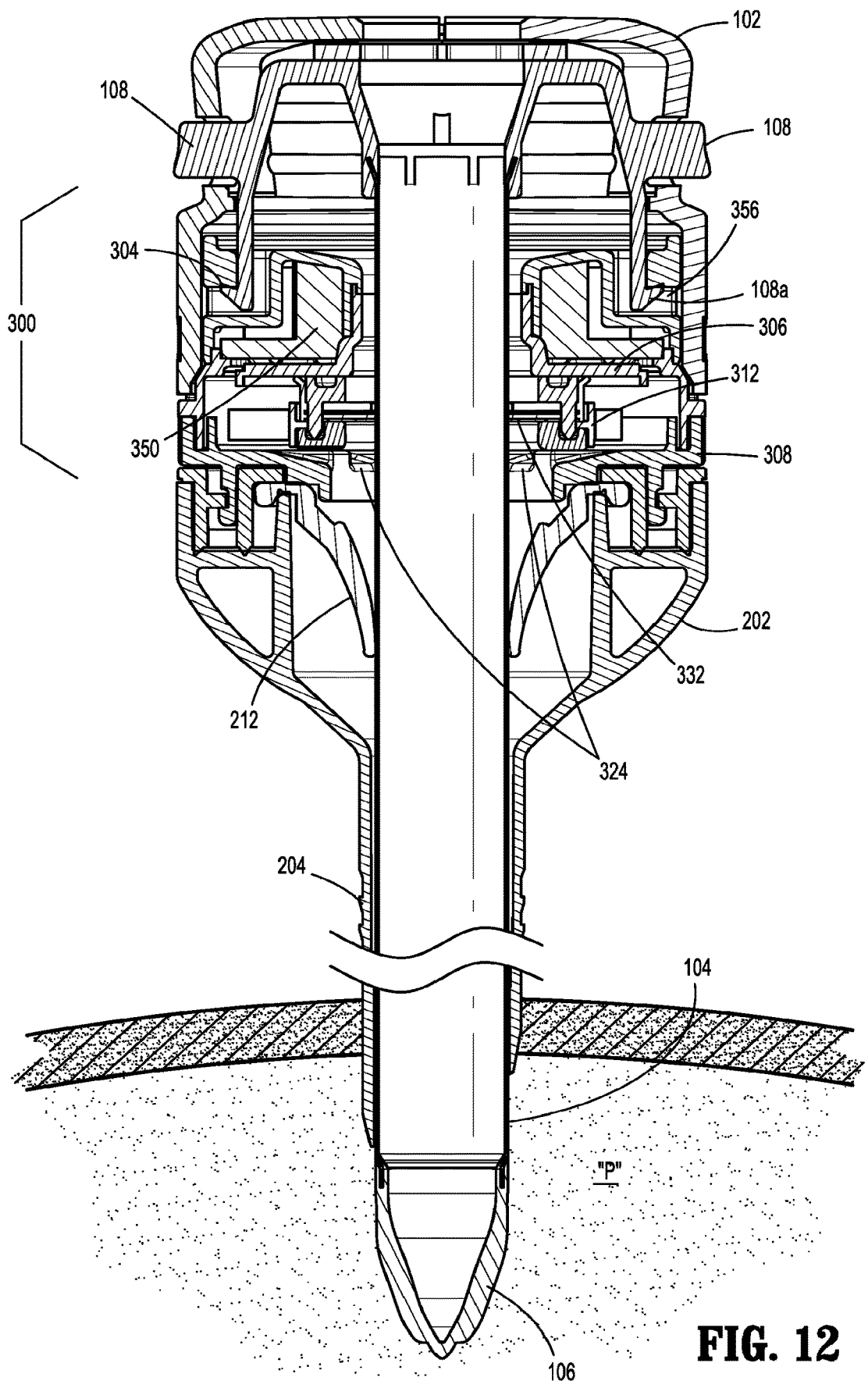
FIG. 12 is a cross-sectional view of the trocar apparatus accessing the peritoneal cavity.

The use of the seal assembly 300 in conjunction with a laparoscopic surgical procedure will be discussed. The peritoneal cavity is insufflated to establish a pneumoperitoneum as is conventional. With reference to FIG. 12, the seal assembly 300 is assembled to the cannula assembly 200 and to the obturator assembly 100. In one embodiment, the detent legs segments 108a of the latches 108 of the obturator assembly 100 are received within the corresponding latch openings 356 of the proximal housing component 304 to releasably secure the obturator assembly 100 to the seal assembly 300. The seal assembly 300 is releasably secured to the cannula housing 202 of the cannula assembly 200 in the afore-described manner. An endoscope is inserted into the obturator, the distal end of the obturator allowing visualization therethrough and having a shape for gently separating tissue. The assembled trocar apparatus 10 is advanced into the peritoneal cavity "p", e.g., under direct visualization with an endoscope, to access the peritoneal cavity "p".

Figure 13:
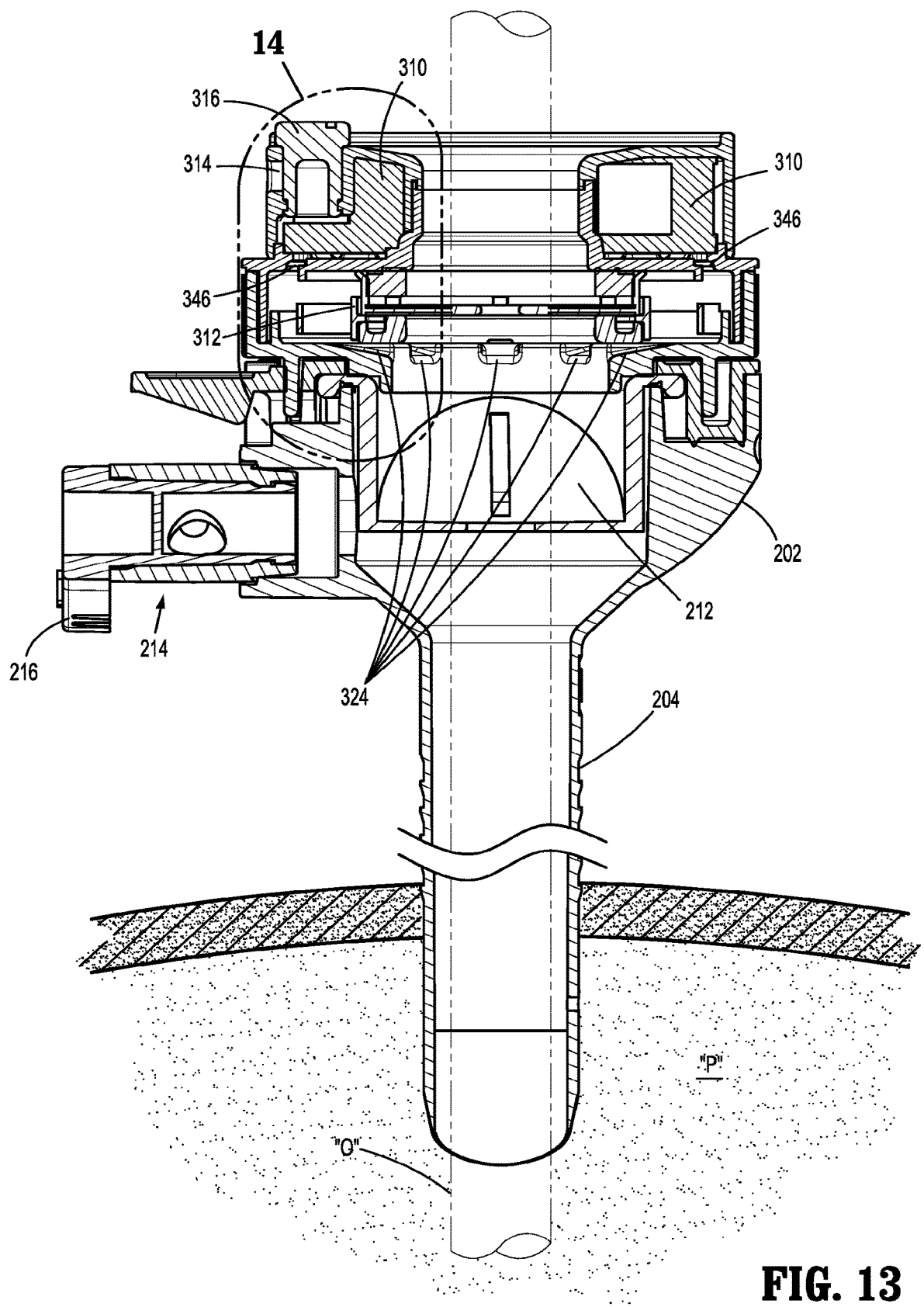
FIG. 13 is a cross-sectional view of the seal assembly mounted to the cannula assembly with a surgical object introduced therethrough.
Figure 14:
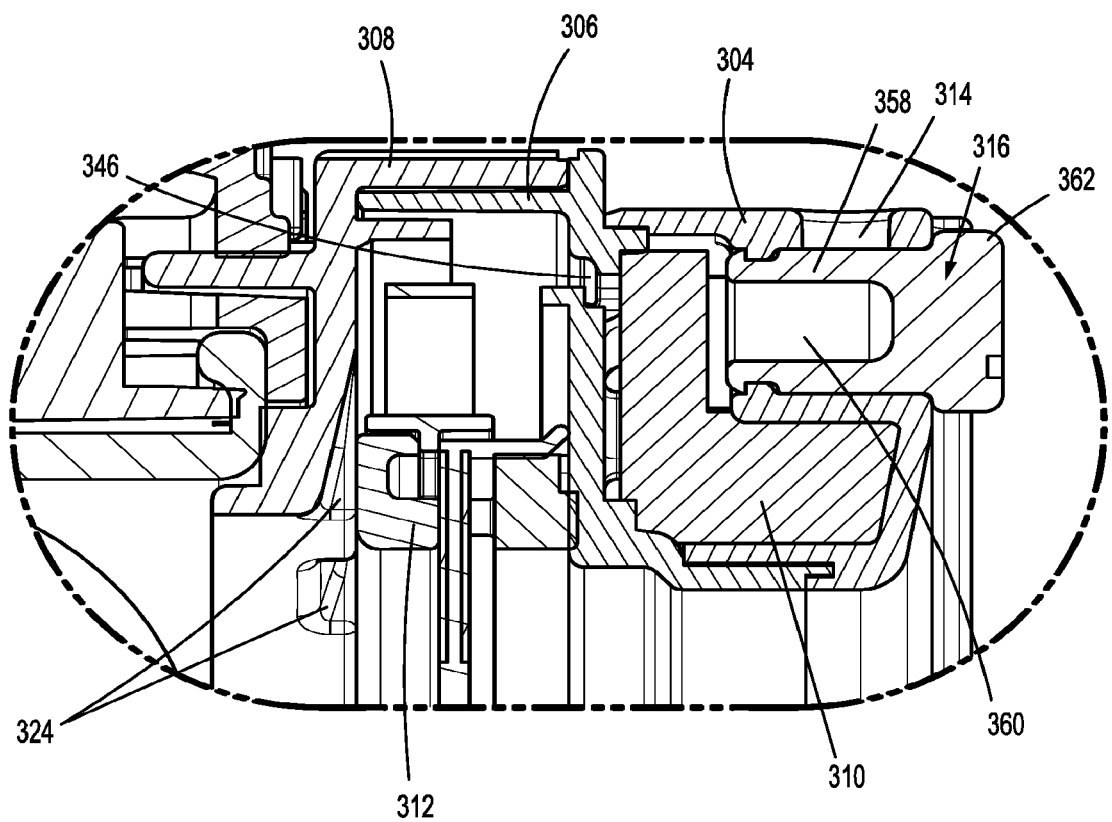
FIG. 14 is an enlarged isolated view of the area of detail of FIG. 13 depicting the evacuation valve in a closed position.
Figure 15:
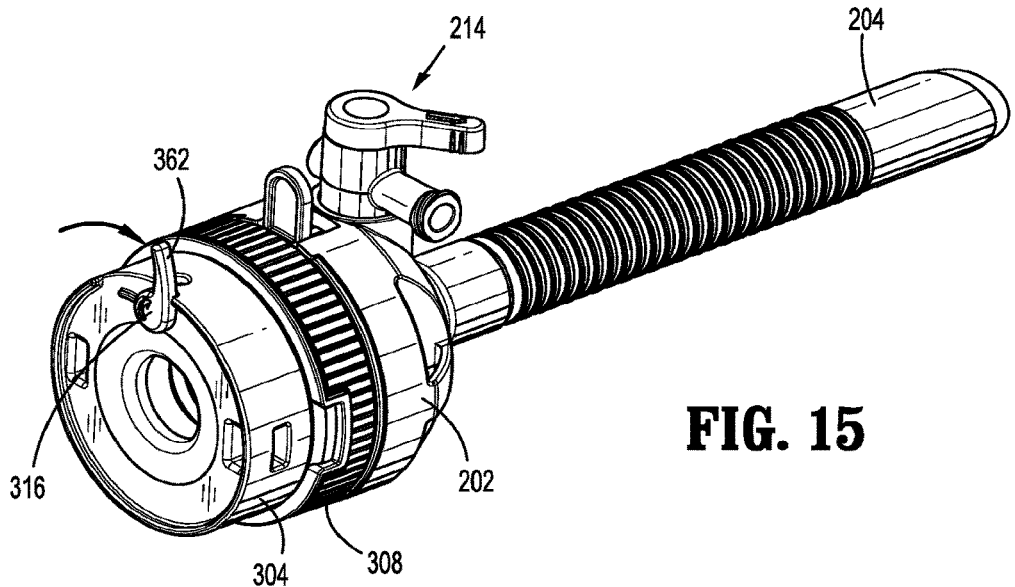
FIG. 15 is a perspective view of the seal assembly and the cannula assembly illustrating manipulation of the evacuation valve to the open position.
Figure 16:
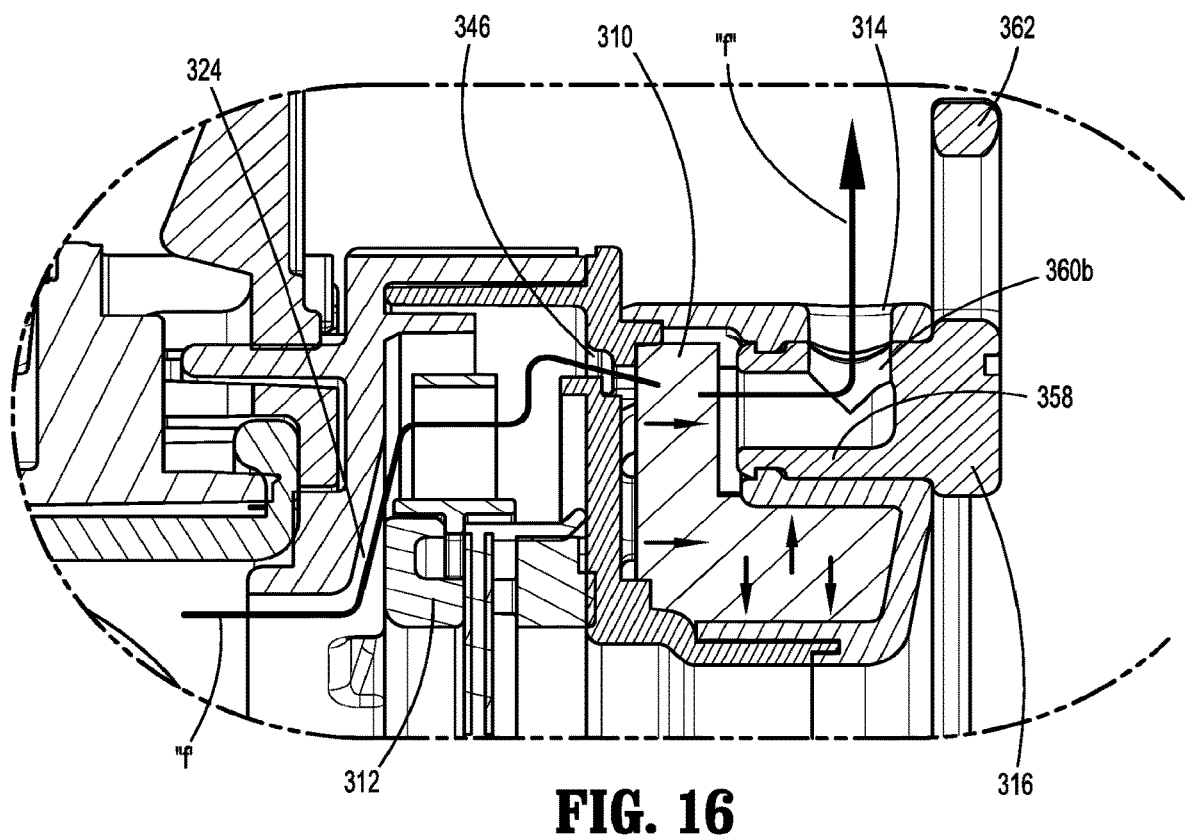
FIG. 16 is a view similar to the view of FIG. 14 illustrating the evacuation valve in an open position and the flow path through the seal assembly and filter for evacuation of smoke and/or other contaminants.

With reference to FIG. 13, the obturator assembly 100 is removed from the seal assembly 300 and the cannula assembly 200. A surgical object "o", e.g., an electro-cautery instrument, is advanced through the seal assembly 300 and the cannula assembly 200. Upon insertion of the surgical object "o", the object seal 312 establishes a sealed relation about the surgical object "o" and the zero closure valve 212 of the cannula housing 202 assumes an open condition. The surgical object "o" may be utilized to perform a surgical task, e.g., cauterization and/or cutting of tissue within the peritoneal cavity "p". Initially, the evacuation valve 316, which may be a simple on/off valve, is in the closed position detailed in FIG. 14 whereby the radial bore segment 360b of the valve bore 360 is offset relative to the evacuation port 314 to prevent egress of fluids. When it is determined to evacuate the contaminated fluids (including smoke and/or contaminants) from within the peritoneal cavity "p", the evacuation valve 316 is rotated as shown in FIG. 15 to the open position via manipulation of the manual member 362 as guided by the directional arrow "a". As best depicted in FIG. 16, in the open position, the radial bore segment 360b of the valve bore 360 of the valve stem 358 is in alignment with the evacuation port 314. The pressure differential between the insufflated peritoneal cavity "p" and the ambient environment causes the contaminated fluids to flow through the cannula sleeve 204 and the zero closure valve 212 (e.g., between spaces defined between the zero closure valve 212 and the inserted surgical object "o"). The contaminated fluids continue along a flow path "f" within the seal housing 302 and defined by the flow channels 324 of the distal housing component 308, around the periphery of the object seal 312, the flow openings 346 of the intermediate housing component 306, and the filter 310. The contaminated fluids are circulated within the filter 310 to remove smoke and other contaminants. The filtered fluids eventually exit through the valve bore 360 of the evacuation valve 316 and out the evacuation port 314. Release of the fluids may be effected even in the presence of a surgical object and independent of operation of the insufflation port 214 and associated insufflation valve 216 of the cannula housing 202. In other examples, the port 314 can be attached to the hospital operating room vacuum system or other source of a vacuum.

Figure 17A:
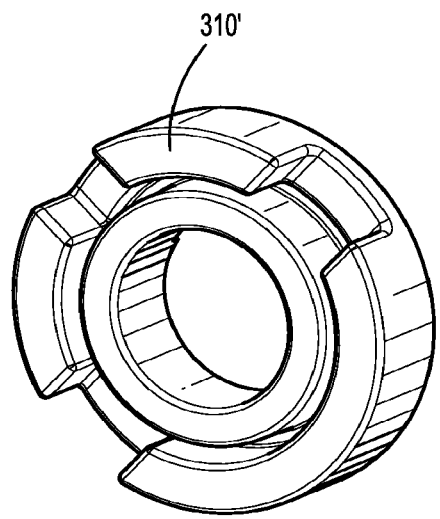
FIGS. 17A-17B are perspective views of one embodiment of the filter of the seal assembly.
Figure 17B:
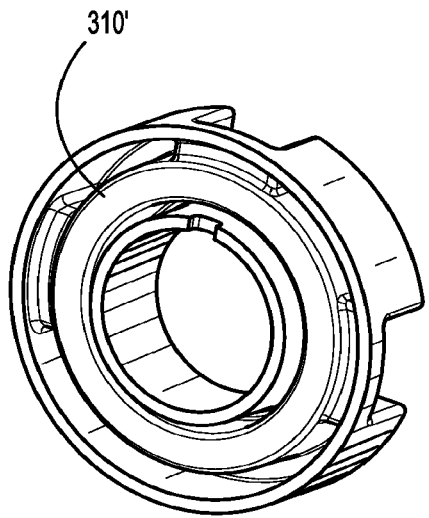

FIGS. 17A-17B illustrate one embodiment of the filter which may be incorporated with the seal assembly 300. The filter 310' comprises a polyurethane foam material having a reticulated, open-pore composition. This filter may be molded to any number of configurations to reside within the seal housing 302. The filter 310' can be a polymeric material with carbon incorporated into it and molded into a shape, such as that shown in FIGS. 17A and 17B. The greater the combined surface area of the filter, the greater capacity and the less resistance to flow. For example, 4-8 square inches of combined surface area in the filter is desired.

In one example, a glass filter material incorporating a carbon material was used. That material was found to be hydrophilic. A polytetra-fluoroethylene ("PTFE") material incorporating carbon was also used. That material was found to be hydrophobic. Since the surgical field is a very wet environment, the hydrophobic material was preferred, as the hydrophobic material tended to clog less.

The filter may be made from carbon incorporated into a polymer resin, granular carbon incorporated in a sheet, a fabric that was a spun-fiber material impregnated with carbon, or any other appropriate material.

In further examples, the filter can be a material incorporating carbon, and including an ULPA material. For example, the carbon material can be molded into a shape as shown in FIG. 17A or 17B, and also have a layer of ULPA material on the top, the bottom, both the top and the bottom, or otherwise disposed adjacent the carbon filter element. In addition, the filter can be made from ULPA filter material that comes in a sheet, and is shaped and folded so as to have folds or pleats, like the filter element shown in FIG. 5. In addition, that filter element can have a layer of carbon material on top, on the bottom, on both the top and bottom, or otherwise disposed alongside the ULPA filter element.

Figure 18:
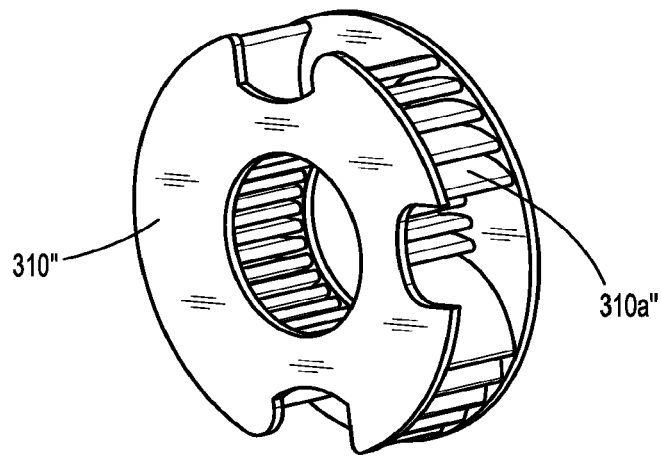
FIG. 18 is a perspective view of another embodiment of the filter of the seal assembly.

FIG. 18 illustrates one embodiment of the filter 310" which also may be incorporated with the seal assembly 300 incorporating arcuate shape pleats or folds 310a". The arcuate pleats 310a", arranged in the curved configuration may increase or maximize filtration area for a given filter size. As shown, the pleats are arranged in a radial direction, extending outwardly from a central longitudinal axis of the cannula. In addition, the pleats 310a" can be evenly spaced around a central axis 333' of the filter, or arranged asymmetrically. For example, through the asymmetrical spacing of the pleats, space can be provided within the housing component for other components such as the evacuation valve 316. Also, the filter may desirably have an upper and lower support 310'.

In a further example, a filter is provided in an access assembly, either inside the cannula assembly seal housing, or as a separate component that has a housing that attaches to the seal housing, or located elsewhere in the cannula assembly, or even alongside it. In a further example, the filter has multiple stages, one of the stages is a HEPA filter and the other stage is an ULPA filter, or a HEPA filter element, an ULPA filter element, and a carbon filter element, or any combination of two or more of them. This can prolong the longevity of the access assembly and desirably impact the effectiveness of the filter.

In a further example, an apparatus to sterilize outflow of abdominal gasses is contemplated for use with an access assembly having a filter arrangement as discussed above or similar to that discussed above, or in conjunction with a separate filtering apparatus. Recent advances in light emitting diode ("LED") technology have reduced the cost of UV-C LED's, (wavelengths of 100-280 NM). This wavelength is known to have a germicidal effect. Using these UV-C LED's sterilizing outflow of abdominal gasses, in conjunction with use of mechanical filter(s) currently in use or as an alternative to such filter(s), can filter out pathogens and bacterium from the abdominal gasses being vented into the operating room theater. This can reduce or eliminate risks to clinicians, operating room staff and/or patients. Another example could use this technology in a UV-Safe abdominal liner, or specimen bag during tissue morcellation to reduce or eliminate the risk associated with mechanical morecellation of tissue(s). In another example, such technology can be used to sterilize tissue contacting devices during insertion through a trocar. The UV-C light, in the form of one or more LED or otherwise, can render pathogens inert, and reduce the flow restriction of any filter being used. This can increase the longevity of any filter being used. This also has the potential of reducing the bio-hazardous waste generated during a procedure.

Figure 19:
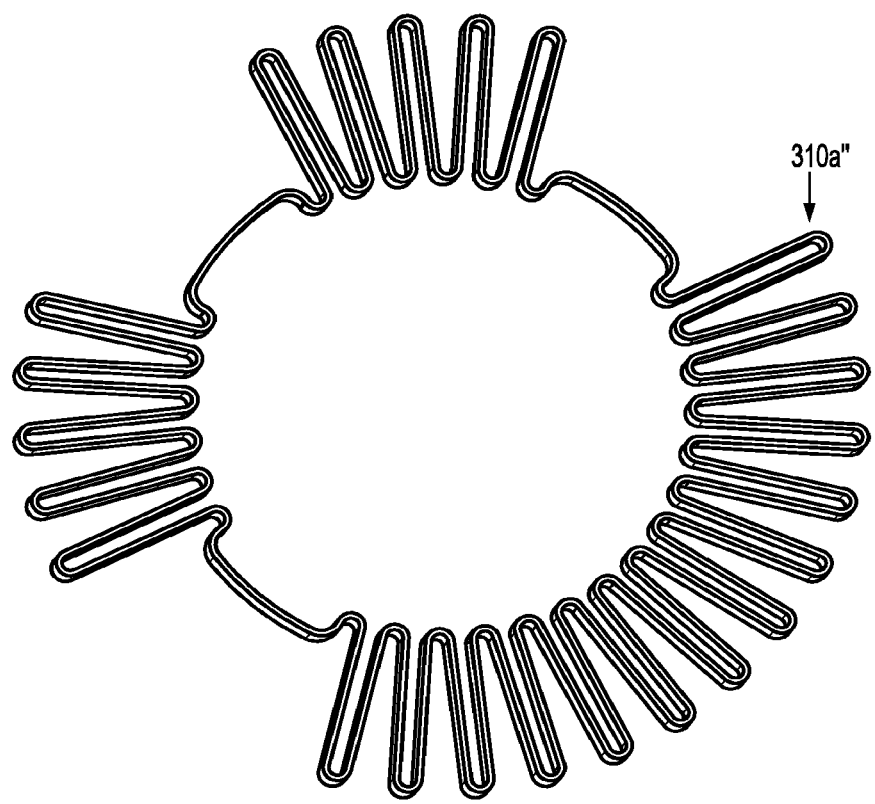
FIG. 19 is a plan view of a filter element having multiple pleats.

FIG. 18 illustrates one embodiment of the filter 310" which also may be incorporated with the seal assembly 300 incorporating arcuate shape pleats 310a". The arcuate pleats 310a", arranged in the curved configuration may increase or maximize filtration area for a given filter size. As shown, the pleats are arranged in a radial direction, extending outwardly from a central longitudinal axis of the cannula. In addition, the pleats 310a" can be evenly spaced around a central axis 333' of the filter, or arranged asymmetrically. (See FIG. 19, which shows the filter material in a plan view). For example, through the asymmetrical spacing of the pleats, space can be provided within the housing component for other components such as the evacuation valve 316. Also, the filter may desirably have an upper and lower support 310'.

Figure 20:
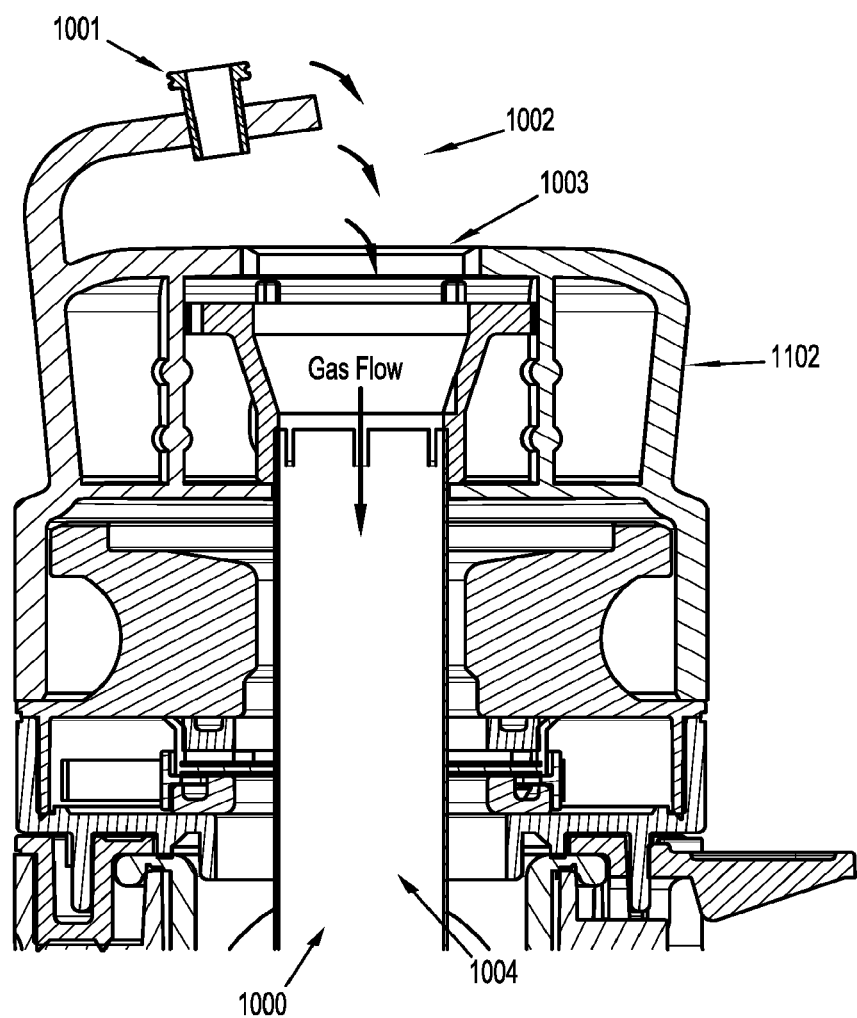
FIG. 20 is a cross-sectional view of a cannula assembly, in partial view, in accordance with an aspect of the present disclosure.
Figure 21:
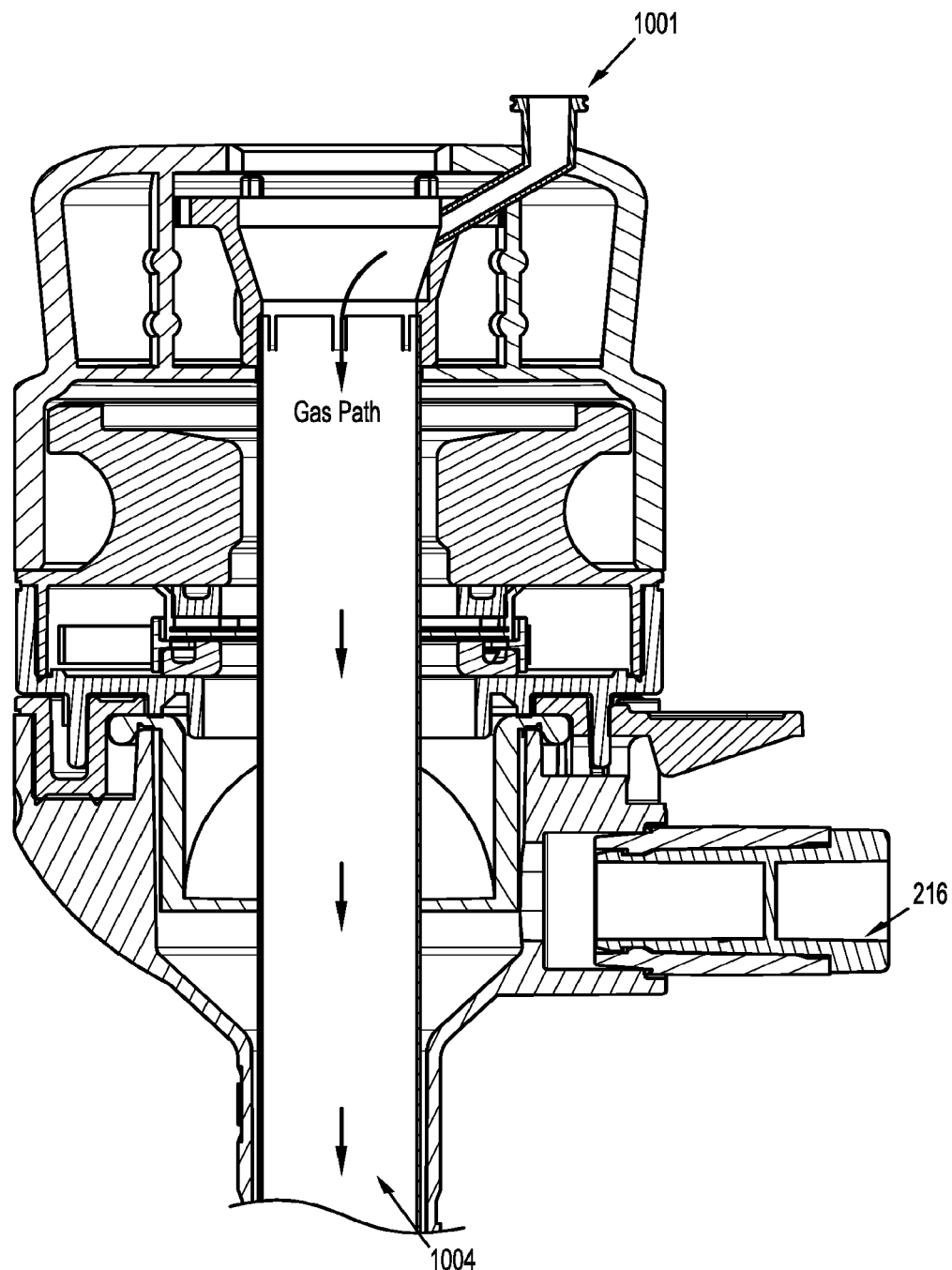
FIG. 21 is the cross-sectional view of the cannula assembly shown in FIG. 20, in partial view.
Figure 22:
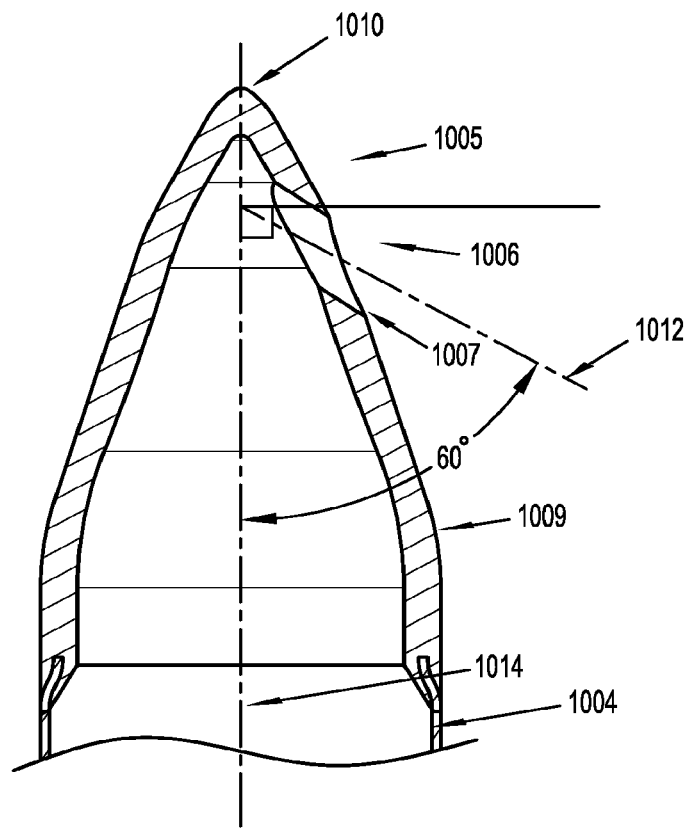
FIG. 22 is a cross-sectional view of an obturator tip in accordance with a further aspect of the present disclosure.

In a further example, the access apparatus can omit the insufflation valve 216 discussed above. As shown in FIG. 22, obturator assembly 1000 has an internal passage for introduction of insufflation gases, and a luer 1001 connection attached to obturator handle 1102. The luer 1001 can be attached to a movable top 1002 attached to obturator handle 1102 so that the top can be snapped onto or otherwise attached to the handle 1102 over the opening 1003. (see FIG. 20) The opening can also be shaped for reception of an endoscope. When attached to a source of insufflation gas, the luer 1001 allows the flow of such gas into the obturator, down the shaft 1004 (FIG. 21), into the abdominal cavity. A distal end 1005 of the obturator has an opening 1006 for this purpose. (See FIG. 22).

To avoid coring of tissue, or the clogging of the interior of the obturator, the distal opening 1006 has an angular shape. As shown in FIG. 22, the opening 1006 is defined by a passage 1007 through the wall 1009 of the distal tip 1010 of the obturator. The central axis 1012 of the passage 1007 has an angle of about 60 degrees with the longitudinal axis 1014 of the shaft 1004 of the obturator. The passage is angled away from the distal end 1005 of the obturator. The angle for axis 1012 can vary from about 20 to about 70 degrees. As the insufflating obturator has a flow path separate from the flow path of the evacuation of gases, fumes, etc., the insufflation obturator can be used in conjunction with the filter, evacuation valve 316, and associated assembly.

Figure 23:
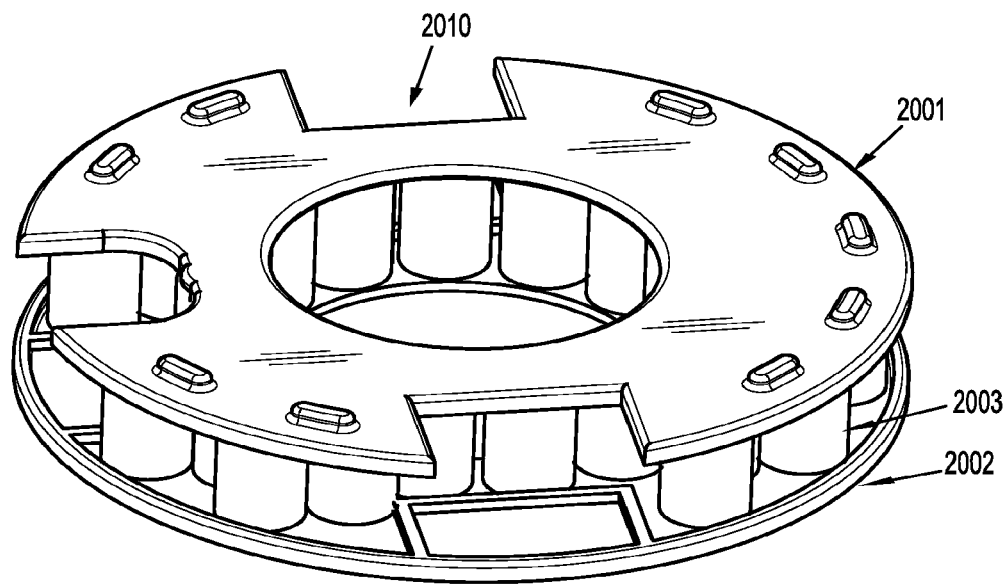
FIG. 23 is a perspective view of a filter element having multiple cylindrical elements in accordance with another example of the present disclosure.

In a further example, the access assembly can be any of the embodiments discussed above, with an alternative filter assembly provided in the seal housing, a separate attachable housing, or located elsewhere in a flow path from inside the insufflated space. As shown in FIG. 23, the filter assembly can have an upper and a lower support 2001, 2002, and a plurality of tubular members 2003. The tubular members may be all the same size and shape, or the size and shape can vary. The tubular members 2003 can be made of the filter materials discussed above, and can involve a single layer of material forming a cylinder, or can be formed from a coil of such material, coiled around in multiple turns. The material can be different in the different tubular members, or can be composite materials. As discussed above, the filter can be symmetrical, or it can be asymmetrical forming spaces 2010 to accommodate other components in the housing component.

Figure 24:
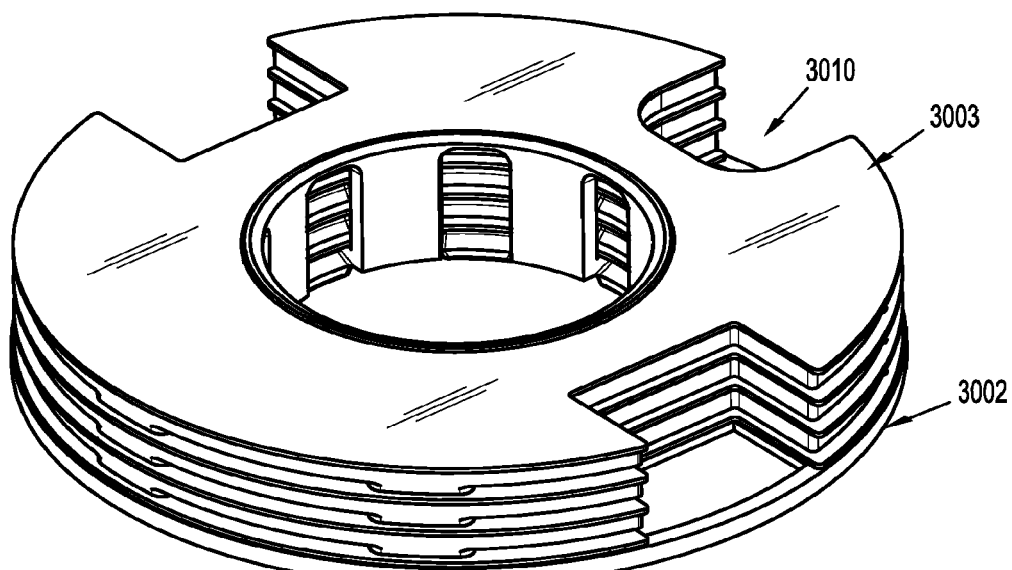
FIG. 24 is a perspective view of a filter element having multiple layers in accordance with another example of the present disclosure.

In a further example, the access assembly can be any of the embodiments discussed above, with another alternative filter assembly. As shown in FIG. 24, the filter assembly can have an upper support (not shown) and a lower support 3002, and a plurality of layer members 3003. The layer members may be all the same size and shape, or the size and shape can vary. The layer members 3003 can be made of the filter materials discussed above, and can involve a single layer of material forming a layer, or can be formed from one or more layers, or one or more coils of such material. The material can be different in the different layer members, or can be composite materials. As discussed above, the filter can be symmetrical, or it can be asymmetrical forming spaces 3010 to accommodate other components in the housing component.

Figure 25:
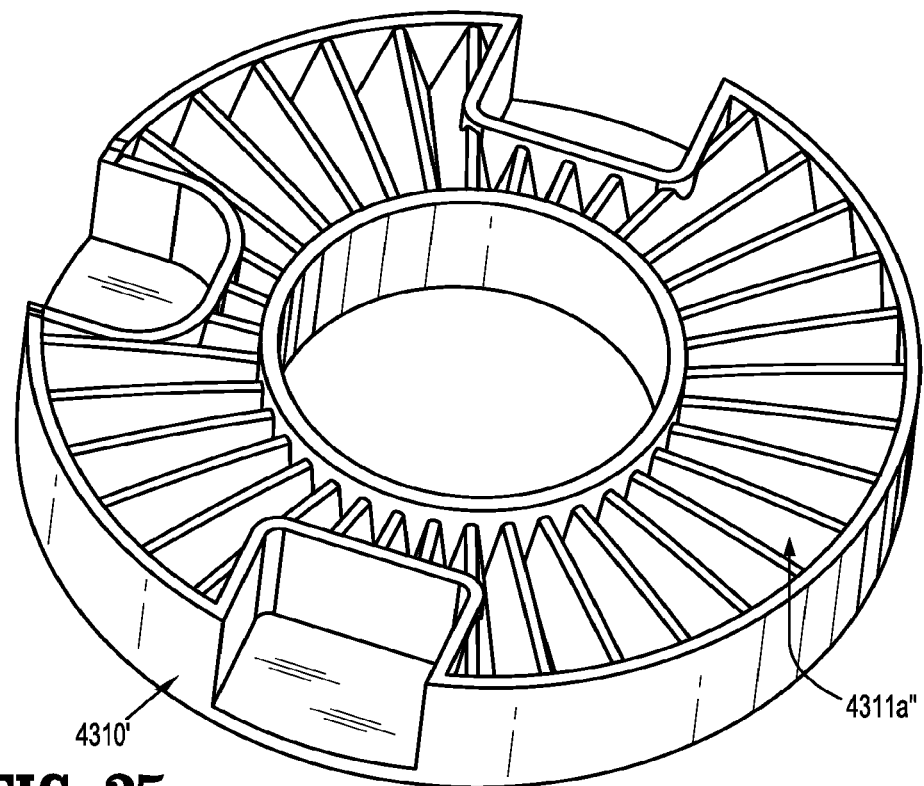
FIG. 25 is a perspective view of a filter element having multiple folds in accordance with another example of the present disclosure.

FIG. 25 illustrates one embodiment of the filter 310" which also may be incorporated with the seal assembly 300 incorporating accordion folds 4311*a*". The folds 4311*a*", arranged to may increase or maximize filtration area for a given filter size. As shown, the folds are arranged in a vertical direction, extending generally upwardly. In addition, the folds 4311*a*" can be evenly spaced around a center of the filter. In addition, space can be provided within the housing component for other components such as the evacuation valve 316. Also, the filter may desirably have an upper and lower support 4310'.

Figure 26:
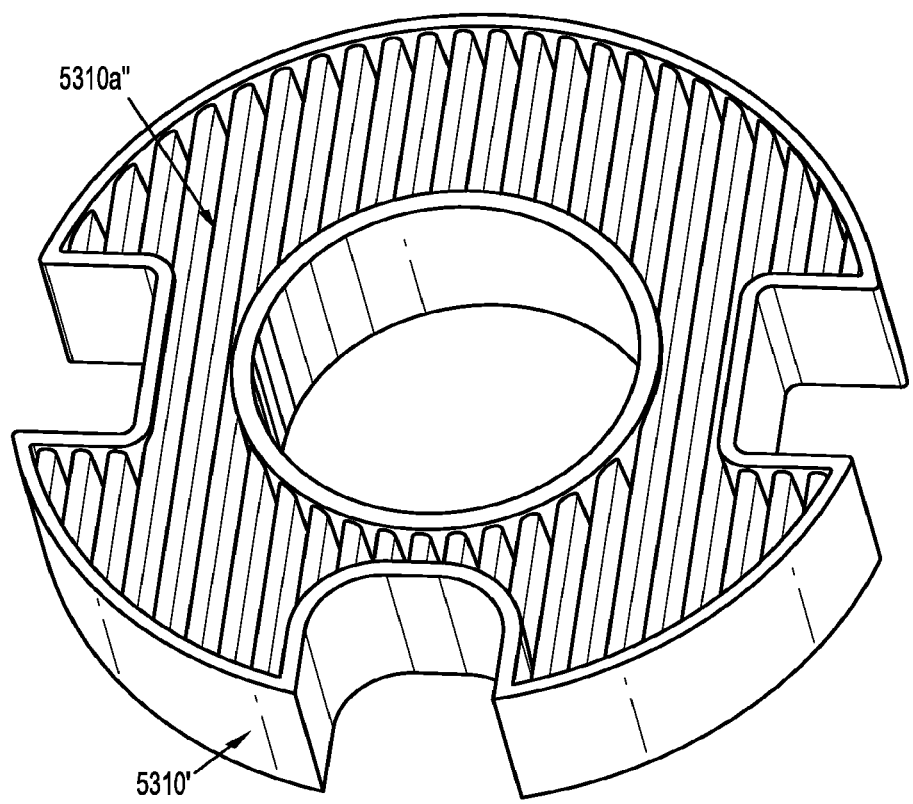
FIG. 26 is a perspective view of a filter element having multiple folds, in a further example, in accordance with another example of the present disclosure.

FIG. 26 illustrates one embodiment of the filter 310" which also may be incorporated with the seal assembly 300 incorporating vertical pleats 5310*a*". The pleats 5310*a*", arranged a configuration to increase or maximize filtration area for a given filter size. As shown, the pleats are arranged in a vertical direction. In addition, the pleats 5310*a*" can be evenly spaced across the filter. In addition, space can be provided within the housing component for other components such as the evacuation valve 316. Also, the filter may desirably have an upper and lower support 5310'.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical cannula assembly comprising:
a seal housing including at least one seal configured to engage a surgical instrument in a sealing relation, the seal housing including a distal housing component defining a plurality of flow channels radially spaced relative to a central axis of the seal housing, the seal housing further including an intermediate housing component configured for at least partially enclosing an object seal, the intermediate housing component defining a plurality of flow openings that communicate with the plurality of flow channels;
a cannula extending distally from the seal housing; and
a filter attachable to the seal housing, the filter disposed in a flow path extending between a distal end of the cannula and an ambient environment through the plurality of flow channels, the filter being proximal of the at least one seal.

2. The surgical cannula assembly according to claim 1, wherein the filter includes first and second supports opposing each other and a plurality of tubular members supported by the first and second supports, each tubular member of the plurality of tubular members including a filter material.

3. The surgical cannula assembly according to claim 2, wherein at least one tubular member of the plurality of tubular members includes the filter material in a coil configuration.

4. The surgical cannula assembly according to claim 2, wherein the plurality of tubular members has a non-uniform filter material.

5. The surgical cannula assembly according to claim 1, wherein the filter is an ultra-high molecular weight filter, an activated carbon filter, or a high efficiency particulate air filter.

6. The surgical cannula assembly according to claim 1, wherein the filter includes a high-density polyethylene material or a polyurethane material, with activated charcoal.

7. The surgical cannula assembly according to claim 1, wherein the filter includes linear or triangular pleats.

8. The surgical cannula assembly according to claim 1, wherein the filter provides a flow rate of at least about 6 liters per minute through the flow path.

9. The surgical cannula assembly according to claim 1, wherein the filter allows up to about 10 liters of small particulate air flow per minute.

10. The surgical cannula assembly according to claim 1, wherein the filter has about 3 to about 10 square inches of combined surface area.

11. A seal assembly for use with a surgical cannula assembly comprising:
a seal housing including a distal housing component defining an axial opening configured for passage of a surgical object therethrough and a plurality of flow channels extending radially outwards relative to the axial opening, the seal housing having an evacuation port;

an object seal configured for sealed reception of the surgical object, the object seal and the seal housing defining a flow path extending proximal of the object seal to permit passage of fluids from an underlying body cavity to exit the evacuation port; and a filter in the seal housing configured for filtering smoke or contaminants from the fluids, the filter disposed proximal of the object seal, wherein the seal housing further includes an intermediate housing component configured for at least partially enclosing the object seal, the intermediate housing component defining a plurality of flow openings that communicate with the plurality of flow channels.

12. The seal assembly according to claim 11, wherein the filter includes multiple pleats of a filter material.

13. The seal assembly according to claim 11, wherein the filter includes multiple layers of filter materials.

14. The seal assembly according to claim 11, wherein the plurality of flow channels of the seal housing are configured to permit passage of fluids about a peripheral segment of the object seal.

15. The seal assembly according to claim 14, wherein the plurality of flow channels are radially spaced relative to a seal axis of the seal housing.

16. The seal assembly according to claim 11, wherein the seal housing includes a proximal housing component for at least partially accommodating the filter, the proximal housing component having the evacuation port.

17. A seal assembly for use with a surgical cannula assembly, the seal assembly comprising:

a seal housing defining an axial opening configured for passage of a surgical object therethrough and a flow channel extending radially outwards relative to the axial opening, the seal housing having an evacuation port, the flow channel including a plurality of flow channels radially spaced relative to a seal axis of the seal housing;

an object seal configured for sealed reception of the surgical object, the object seal and the seal housing defining a flow path extending proximal of the object seal to permit passage of fluids from an underlying body cavity to exit the evacuation port; and a filter including multiple layers of filter materials, the filter positioned in the seal housing and configured for filtering smoke or contaminants from the fluids, the filter disposed proximal of the object seal, wherein the plurality of flow channels of the seal housing are configured to permit passage of fluids about a peripheral segment of the object seal, and the seal housing including an intermediate housing component configured for at least partially enclosing the object seal, the intermediate housing component defining a plurality of flow openings in fluid communication with flow channels of an internal seal mount to permit passage of fluids proximal of the intermediate housing component.

18. The seal assembly according to claim 17, wherein the filter is disposed adjacent the intermediate housing component, the filter being in fluid communication with the plurality of flow openings of the intermediate housing component.

* * * * *